United States Patent
Bazant

(10) Patent No.: US 11,786,840 B2
(45) Date of Patent: Oct. 17, 2023

(54) FILTRATION PROCESS AND ASSEMBLY

(71) Applicant: SAINT-GOBAIN CERAMICS & PLASTICS, INC., Worcester, MA (US)

(72) Inventor: Martin Z. Bazant, Wellesley, MA (US)

(73) Assignee: SAINT-GOBAIN CERAMICS & PLASTICS, INC., Worcester, MA (US)

( * ) Notice: Subject to any disclaimer, the term of this patent is extended or adjusted under 35 U.S.C. 154(b) by 577 days.

(21) Appl. No.: 16/764,806

(22) PCT Filed: Nov. 16, 2018

(86) PCT No.: PCT/US2018/061626
§ 371 (c)(1),
(2) Date: May 15, 2020

(87) PCT Pub. No.: WO2019/099905
PCT Pub. Date: May 23, 2019

(65) Prior Publication Data
US 2020/0398186 A1    Dec. 24, 2020

Related U.S. Application Data

(60) Provisional application No. 62/588,051, filed on Nov. 17, 2017.

(51) Int. Cl.
*B01D 15/02*    (2006.01)
*A61M 1/02*    (2006.01)
*B01J 20/28*    (2006.01)

(52) U.S. Cl.
CPC .......... *B01D 15/02* (2013.01); *A61M 1/0281* (2013.01); *B01J 20/28038* (2013.01)

(58) Field of Classification Search
CPC ....... B01D 33/00; B01D 33/04; B01D 33/048
See application file for complete search history.

(56) References Cited

U.S. PATENT DOCUMENTS 5,866,000 A    2/1999    Veh
9,248,583 B2    2/2016    Tian
(Continued)

FOREIGN PATENT DOCUMENTS

WO        9737776 A1    10/1997
WO    2005035131 A1    4/2005

OTHER PUBLICATIONS

Gans, et al.: "Dip-coating of non-Brownian suspensions", Soft Matter, The Royal Society of Chemistry, Aug. 31, 2018.
(Continued)

*Primary Examiner* — Ryan B Huang
(74) *Attorney, Agent, or Firm* — Abel Schillinger, LLP; Adrian Lawrence

(57) ABSTRACT

A filtering process can comprise providing a dispersion comprising a liquid and a plurality of particles contained in the liquid; moving an object relative to the dispersion; selectively removing at least a portion of the plurality of particles from the dispersion to obtain a plurality of separated particles attached to the object. In a further embodiment, an assembly for separating particles from a dispersion can comprise a chamber including a dispersion, the dispersion comprising a liquid and a plurality of particles; a movable object, the object being adapted for moving through the chamber and adsorbing at least a portion of the plurality of particles during moving; a first construction adapted for moving the object relative to the dispersion at a controlled moving speed, and a second construction adapted for removing and collecting from the object a plurality of separated particles from the dispersion.

17 Claims, 26 Drawing Sheets

(56) References Cited

U.S. PATENT DOCUMENTS

| | | |
|---|---|---|
| 2005/0158452 A1 | 7/2005 | Bush |
| 2007/0251383 A1 | 11/2007 | Mueller |
| 2010/0224574 A1* | 9/2010 | Youngs ............... B01D 33/646 |
| | | 210/780 |
| 2011/0293851 A1 | 12/2011 | Bollstroem |
| 2012/0222558 A1 | 9/2012 | Maskrot |
| 2015/0004360 A1* | 1/2015 | Mengerink ............ G01N 33/48 |
| | | 428/137 |

OTHER PUBLICATIONS

Sauret, et al.: "Capillary filtering of particles during dip coating", www.pnas.org/cgi/doi/10.1073/pnas.XXXXXXXXXX, Aug. 7, 2018.

Colosqui, et al.: "Hydrodynamically Driven Colloidal Assembly in Dip Coating", Phys Rev. Lett. 110, 188302—Published Apr. 30, 2013.

C. Jeffrey Brinker, "Chapter 10, Dip Coating", T. Schneller et al. (eds), Chemical Solution Deposition of Functional Oxide Thin Films, DOI 10.1007/978-3-211-99311-8_10, © Springer-Verlag Wien 2013.

Sauret, et al.: "Dip-coating in a suspension: entrainment of particles", Abstract Submitted for the DFD17 Meeting of The American Physical Society, Aug. 1, 2017.

Yingxian Yu, et al.: "Bubbles as leaky pistons: extracting small particles from polydisperse suspensions", Abstract Submitted for the DFD17 Meeting of The American Physical Society, Oct. 2, 2017.

Colosqui, et al.: "Hydrodynamically-driven colloidal assembly in the thin—lm entrainment regime", arXiv:1209.51472 [physics.flu-dyn] Oct. 1, 2012.

International Search Report & Written Opinion, dated Apr. 29, 2020 with regard to International Application No. PCT/US2018/061626.

* cited by examiner

FILTRATION PROCESS AND ASSEMBLY

CROSS-REFERENCE TO RELATED APPLICATIONS

This application is the National Stage of International Application No. PCT/US2018/61626, entitled "FILTRATION PROCESS AND ASSEMBLY", by Martin Z. BAZANT, filed Nov. 16, 2018, which claims priority under 35 U.S.C. § 119(e) to U.S. Patent Application No. 62/588,051, entitled "FILTRATION PROCESS AND ASSEMBLY", by Martin Z. BAZANT, filed Nov. 17, 2017, of which both applications are assigned to the current assignee hereof and incorporated herein by reference in their entireties.

TECHNICAL FIELD

The present disclosure relates to a filtering process of selectively removing particles from a dispersion and an assembly for conducting the filtering.

BACKGROUND ART

Separating small particles in a micron-size range (up to 1000 microns) from a liquid dispersion provides ongoing challenges. With decreasing particle size and increasing volume of the production batches, most filtering methods are not very efficient and suitable for a large throughput and/or are not highly selective. For example, the use of mechanical filters of a specific pore size can quickly lead to clogging of the filter pores and slowing down of the filtering process. If centrifugation is used as filtering method, the particles are not separated with a high selectivity, and each fraction can contain particles which are not wanted.

There is an ongoing need to develop improved filtering methods having a desired cutoff size in a time efficient and continuous manner.

SUMMARY

According to one embodiment, a filtering process comprises: providing a dispersion comprising a liquid and a plurality of particles contained in the liquid; moving an object relative to the dispersion; selectively removing at least a portion of the plurality of particles from the dispersion to obtain a plurality of separated particles in a liquid film effectively attached to the object; and removing the separated particles from the object.

According to another embodiment, a filtering process comprises: providing a dispersion comprising a liquid and a plurality of particles contained in the liquid; moving an object relative to the dispersion; and controlling at least one parameter selected from the group consisting of a viscosity of the dispersion; a surface tension of the dispersion; a moving speed of the object; a shape of the object; and a dimension of the object, wherein controlling is conducted to selectively remove at least a portion of the plurality of particles from the dispersion to obtain a plurality of separated particles attached to a surface of the object.

According to yet another embodiment, a filtering process comprises: providing a dispersion comprising a liquid, a first plurality of particles contained in the liquid, and a second plurality of particles contained in the liquid, the second plurality of particles being distinct from the first plurality of particles based upon at least one characteristic selected from the group consisting of average particle size (D50), D90 particle size, D10 to D90 size range value, particle shape, and chemical composition of the particles; moving an object through the dispersion; and controlling at least one parameter selected from the group consisting of viscosity of the dispersion, surface tension of the dispersion, moving speed of the object, shape of the at least, and dimension of the object, wherein controlling is conducted to selectively remove from the dispersion at least a portion of the first plurality of particles or at least a portion of the second plurality of particles to obtain a plurality of separated particles attached to a surface of the object.

In another embodiment, a filtering process comprises: providing a dispersion comprising a liquid and a plurality of particles contained in the liquid; moving at least one object relative to the bulk dispersion; and controlling at least one parameter selected from the group consisting of a viscosity of the dispersion, a surface tension of the dispersion, a moving speed of the at least one object, a shape of the at least one object; and a dimension of the at least one object, wherein controlling is conducted to selectively remove the liquid from the dispersion on a surface of the object to obtain a separated liquid, the separated liquid being essentially free of the plurality of particles contained in the dispersion.

In a further embodiment, an assembly for separating particles from a dispersion comprises: a chamber including a dispersion, the dispersion comprising a liquid and a plurality of particles; a movable object, the object being adapted for moving through the chamber and adsorbing at least a portion of the plurality of particles during moving; a first construction adapted for moving the object relative to the dispersion at a controlled moving speed, and a second construction adapted for removing and collecting from the object a plurality of separated particles from the dispersion.

BRIEF DESCRIPTION OF THE DRAWINGS

The present disclosure may be better understood, and its numerous features and advantages made apparent to those skilled in the art by referencing the accompanying drawings.

DETAILED DESCRIPTION OF THE PREFERRED EMBODIMENT(S)

Figure 1:
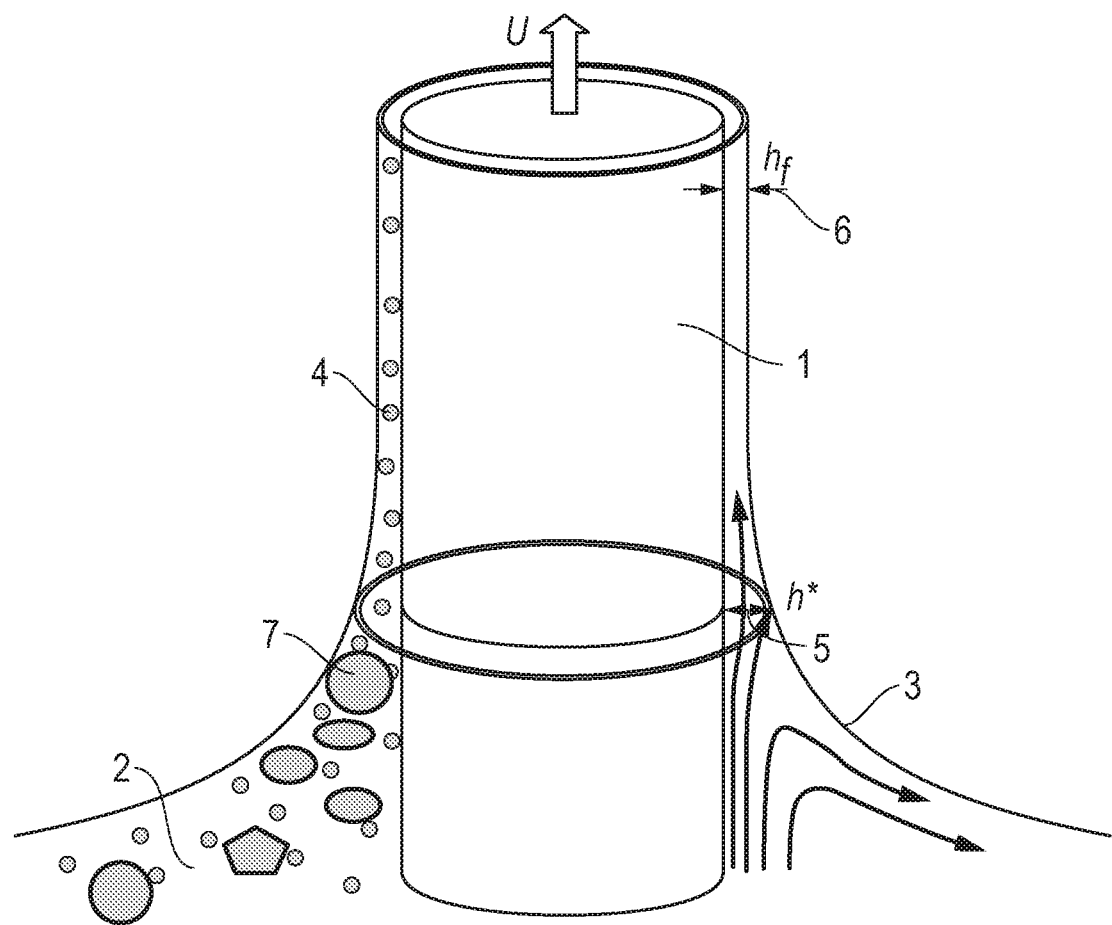
FIG. 1: includes an illustration of the filtering principle along a moving wire according to one embodiment.

As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus.

As used herein, and unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

Also, the use of "a" or "an" are employed to describe elements and components described herein. This is done merely for convenience and to give a general sense of the scope of the invention. This description should be read to include one or at least one and the singular also includes the plural unless it is obvious that it is meant otherwise.

As used herein, the term "dispersion" is intended to mean a combination of a liquid with solid particles and optional further additives, and has the flow characteristic of a liquid. The dispersion of the present disclosure can be a suspension, an emulsion, or a colloidal dispersion.

Various embodiments of the present disclosure will now be described, by way of example only, with reference to the accompanying drawings.

The present disclosure relates to a filtering process which can selectively remove particles from a dispersion by attaching them to the surface of an object when moving the object relative to the dispersion, and removing in a second step the separated particles from the object.

The filtering process of the present disclosure can make use of capillary force phenomena between a liquid dispersion and a solid surface of an object, and by controlling process parameters according to a mathematical theory. As illustrated in the embodiment shown in FIG. 1, when pulling an object (1) out of a dispersion (2), the dispersion may form a dynamic meniscus (3) along the moving surface of the object (1). The capillary forces of the dynamic meniscus can allow particles $P_s$ (4) contained in the dispersion with a particle size smaller than the thickness of the dynamic meniscus at a stagnation point h* (5) being removed and separated from the dispersion by being included in a liquid film (6) that maintains on the object after withdrawal from the dispersion. The stagnation point h* (5) can be considered as the height of the dynamic meniscus wherein capillary forces and gravitational forces are in an equilibrium, and particles $P_1$ (7) larger than a thickness of the meniscus at the stagnation point (5) cannot enter the film (6) removed by the object (1).

The thickness of the meniscus at the stagnation point h* (5) may be influenced and varied by several parameters, for example, the viscosity of the dispersion, the surface tension of the dispersion, the moving speed of the object, the shape of the object, and a dimension of the object. The method of the present disclosure can achieve a surprisingly highly selective separation of particles from a dispersion up to a certain particle size cut, which is hereafter also called cutoff size, by controlling one or more of the above-listed parameters.

In one embodiment, the method of the present disclosure includes removing the separated particles from the surface of the object. In a particular embodiment, the separated particles can be removed from the object, for example, by washing the surface of the object with a collecting fluid such that the separated particles be contained in the collecting fluid after washing. In another embodiment, the liquid film including the separated particles can be evaporated by a drying step. After drying, the separated particles can be easily removed from the object, for example, by a brush, a knife, or guided air blowing.

The process of the present disclosure has the advantage that it can be conducted as a continuous process.

In the filtering process of the present disclosure, controlling of at least one of the above-cited parameters can include adjusting the parameters during the filtering. Adjusting can include measuring at least one parameter during the moving of the object through the dispersion and generating a measurement value, and changing at least one parameter during moving of the object through the dispersion based on the measured value. The measured value can be at least one of a viscosity value, a surface tension value, a moving speed value, a shape value, a dimension value, a cutoff size value, or any combination thereof. In one embodiment the capillary number can be calculated based on one or more measurement values, and at least one parameter may be changed based on the capillary number. In a further embodiment, the measurement value can be associated with a thickness of the film formed on the object during filtering and at least one parameter may be changed based on the measurement value associated with the thickness of the film. A summary how calculations can be made using known process parameters to influence another process parameter and to obtain a desired filtering result is demonstrated in the experimental part.

The filtering process of the present disclosure can be designed that the separated particles may have a desired maximum particle size $P_m$, also called herein the cutoff size. In one embodiment, the cutoff size of the plurality of separated particles can be at least 1 μm, such as at least 3 μm, at least 5 μm, at least 10 μm, or at least 15 μm. In another embodiment, the cutoff size may be not greater than 1000

μm, such as not greater than 800 μm, not greater than 500 μm, not greater than 300 μm, not greater than 100 μm, not greater than 50 μm, not greater than 30 μm, or not greater than 20 μm. The cutoff size can be a value between any of the minimum and maximum values noted above, such as from 1 μm to 1000 μm, from 10 μm to 100 μm, or from 12 μm to 20 μm.

The following is a discussion of the process parameters that can be controlled during the filtering process of the present disclosure.

The moving speed of the object can be at least 0.0005 m/s, such as at least 0.001 m/s, or 0.002 m/s. In another aspect, the at least the moving speed of the object can be not greater than 3 m/s, such as not greater than 2.2 m/s, not greater than 1.5 m/s, or not greater than 1 m/s. The moving speed can be a value between any of the minimum and maximum number noted above, such as from 0.0005 m/s to 3 m/s, from 0.001 m/s to 2.2 m/s, or from 0.002 m/s to 1 m/s.

In one embodiment, the viscosity at 25° C. of the dispersion may be at least 0.2 cP, such as at least 0.3 cP, or at least 0.4 cP. In another embodiment, the viscosity can be not greater than 50 cP, such as not greater than 30 cP, not greater than 20 cP, not greater than 10 cP, not greater than 8 cP, not greater than 6 cP, not greater than 5 cP, or not greater than 4 cP. The viscosity can be a value between any of the minimum and maximum values noted above, such as from 0.2 cP to 6 cP, from 0.3 cP to 4 cP, or from 0.5 cP to 2 cP.

In another embodiment, the surface tension of the dispersion of the dispersion may be not greater than 100 mN/m, such as not greater than 80 mN/m, or not greater than 50 mN/m. In yet another embodiment, the surface tension may be at least 10 mN/m, such as at least 15 mN/m, or at least 20 mN/m. The surface tension can be a value between any of the maximum and minimum number noted above, such as from 100 mN/m to 10 mN/m, from 70 mN/m to 17 mN/m, or from 50 mN/m to 20 mN/m.

In one embodiment, the capillary number can be at least 0.0001, such as at least 0.0002, or at least 0.001. In another embodiment, the capillary number Ca may be not greater than 0.04, such as not greater than 0.02, not greater than 0.015, or not greater than 0.012. The capillary number may be a value between any of the minimum and maximum values notes above, such as from 0.0001 to 0.4, from 0.0002 to 0.03, or from 0.001 to 0.15.

As used herein, the term "plurality of particles" is intended to describe particles contained in the dispersion which are not soluble in the liquid. In the context of the present disclosure, the term "plurality of particles" is interchangeable used with the term "the particles contained in the dispersion." Non-limiting examples of particles contained in the dispersion can be abrasive particles, pigments, dyes, polymers, or biological materials. In one aspect, the abrasive particles can include a material selected from diamond, cubic boron nitride, silicon carbide, boron carbide, alumina, silicon nitride, tungsten carbide, zirconia, silica, ceria, or any combination thereof. In other aspects, the biological material can contain whole cells, cell fragments, or micro-organisms, such as red blood cells, white blood cells, platelets, macrophages, dendritic cells, proteins, viruses, bacteria, spores or any combination thereof. The plurality of particles may not be limited to one type or a specific batch of particles, but can include particles from different batches with different particle size distribution, different material type, and/or different shape. Accordingly, the particle size distribution of the plurality of particles can be a monomodal or multimodal distribution, such as bimodal, trimodal, or tetramodal.

The particles contained in the dispersion can have a wide particle distribution range, from about 10 nm up to 5000 μm or larger. Depending on the purpose of the filtering, however, at a particle size above 1000 μm, the filtering process of the present disclosure cannot separate the particles by attaching them on the moving surface of the object. Dispersions containing particles at a size of larger than 1000 μm can be filtered, however, by removing only the liquid via the object, while the particles remain in the dispersion. In another embodiment, removing only the liquid from the dispersion can be conducted also with dispersions containing particles smaller than 1000 μm, wherein process parameters can be selected and controlled that the thickness of the dynamic meniscus at the stagnation point h* is smaller than the size of the particles contained in the dispersion.

In a certain embodiment, the particles of the dispersion can have an average particles size ($D_{50}$) of at least 1 μm, such as at least 3 μm, at least 5 μm, or at least 10 μm, or at least 15 μm. In another aspect, the average particle size can be not greater than 1000 μm, such as not greater than 500 μm, not greater than 200 μm, not greater than 100 μm, not greater than 50 μm, not greater than 30 μm, or not greater than 20 μm. The average particle size of the plurality of particles contained in the dispersion can be a value between any of the minimum and maximum values noted above, such as from 1 μm to 1000 μm, 5 μm to 500 μm, or 10 μm to 100 μm.

In another certain embodiment, the plurality of particles contained in the dispersion can have a $D_{90}$ particles size of at least 2 μm, such as at least 5 μm. In another embodiment, the D90 particle size can be not greater than 2000 μm, such as not greater than not greater than 1500 μm, not greater than 1000 μm, not greater than 800 μm, not greater than 500 μm, not greater than 300 μm, or not greater than 200 μm. The D90 particles size can be a value between any of the minimum and maximum values noted above, such as from 2 μm to 2000 μm, from 10 μm to 400 μm, or from 20 μm to 150 μm.

In one aspect, the amount of particles in the dispersion subjected to the filtering process of the present disclosure can be at least 0.1 vol %, such as at least 0.2 vol %, at least 0.4 vol %, at least 0.8 vol %, or at leas 1 vol %. In another aspect, the amount of particles may be not greater than 30 vol %, such as not greater than 20 vol %, not greater than 15 vol %, not greater than 10 vol %, or not greater than 5 vol %. The amount of particles in the dispersion can be a value between any of the minimum and maximum values noted above.

In one particular embodiment, the dispersion of the present process can include a first plurality of particles and a second plurality of particles, wherein the second plurality of particles can be distinct from the first plurality of particles based upon at least one characteristic selected from the average particle size ($D_{50}$ value), the D90 particle size, the D90–D10 value, the particle shape, and the chemical composition of the particles.

In a particular embodiment, the particle distribution of the plurality of particles contained in the dispersion can be a bimodal particle distribution, wherein one modal has a D10 to D90 size range value from 1 μm to 10 μm, and the other modal has a D10 to D90 size range value from 20 μm to 100 μm. In a further embodiment, the particle distribution can be a monomodal distribution, wherein the D10 to D90 size range value is below the cutoff size, such that all particles can be removed from the dispersion with the object.

In another embodiment, the particle dispersion can include an additive, for example a dispersant, a viscosity modifier, stabilizer, an anti-foaming agent, a surfactant, or any combination thereof.

The liquid film remaining on the object after filtering can contain a significant volume fraction of captured particles. In one embodiment, the volume fraction of captured particles in the liqud film can be at least 0.1%, such as at least 1%, or at least 10%. In another embodiment, the volume fraction of captured particles may be nor greater than 70%, such as not greater than 50%, or not greater than 10%. For spherical particles, random close packing and jamming may occur at around 63%, but higher volume fractions can be possible in slurries of polydisperse dispersions and/or with irregular particle shapes.

In a further embodiment, the filtering method of the present disclosure can have a high flow rate. As used herein, the flow rate relates to the amount of liquid film (including solid particles) attached to the object and removed during filtering from the dispersion in a certain amount of time. In one embodiment, the flow rate can be at least 0.001 L/hour, such as at least 0.005 L/hour, 0.01 L/hour, 0.05 L/lour, or 0.1 L/hour, or 0.3 L/hour, or 0.5 L/hour, or 0.8 L/hour, or 1 L/hour, or 1.2 L/hour. In another aspect, the flow rate may be not greater than 50 L/hour, such as not greater than 30 L/hour, not greater than 20 L/hour, such as not greater than 15 L/hour, or not greater than 12 L/hour, or not greater than 10 L/hour. Much larger flow rates can also be achieved by scaling up the system to include more moving objects with larger total surface area. The flow rate per surface area is approximately constant and equal to the limiting film thickness (calculated below) times the pulling velocity.

Figure 2:
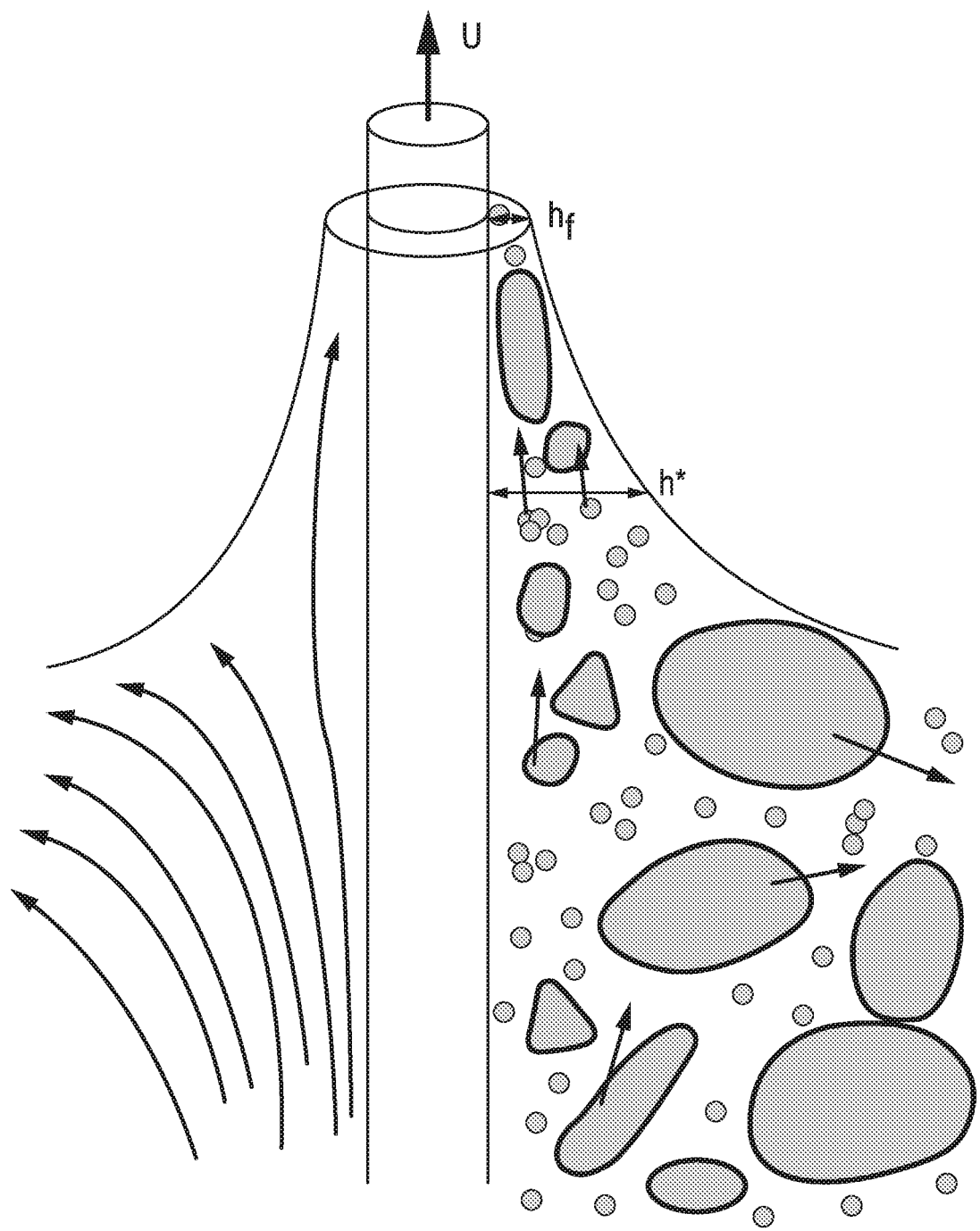
FIG. 2: includes an illustration of forming a film on a cylindrical wire to conduct particle separation according to one embodiment.
Figure 3:
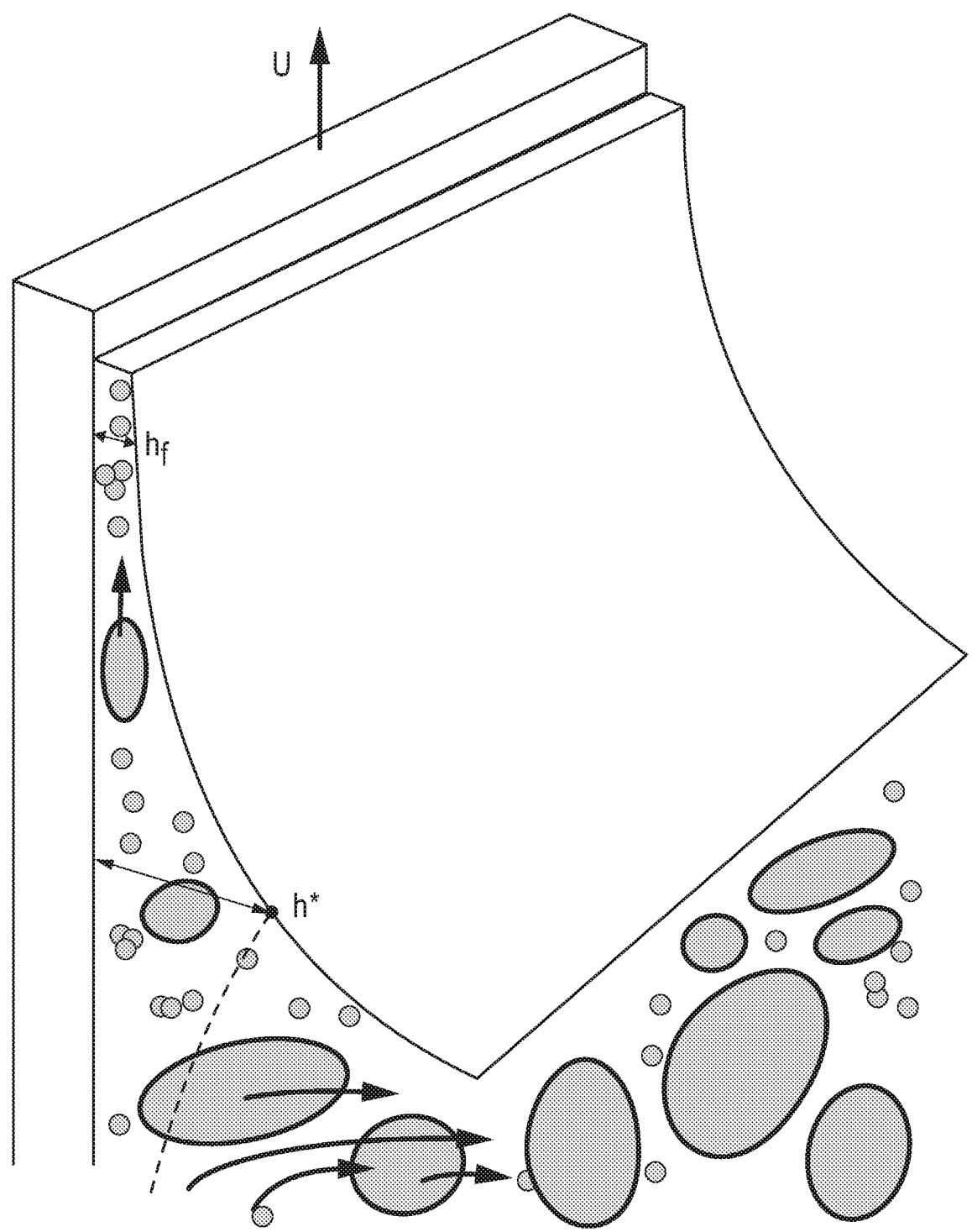
FIG. 3: includes an illustration of forming a film on a flat belt for particle separation according to one embodiment.
Figure 4:
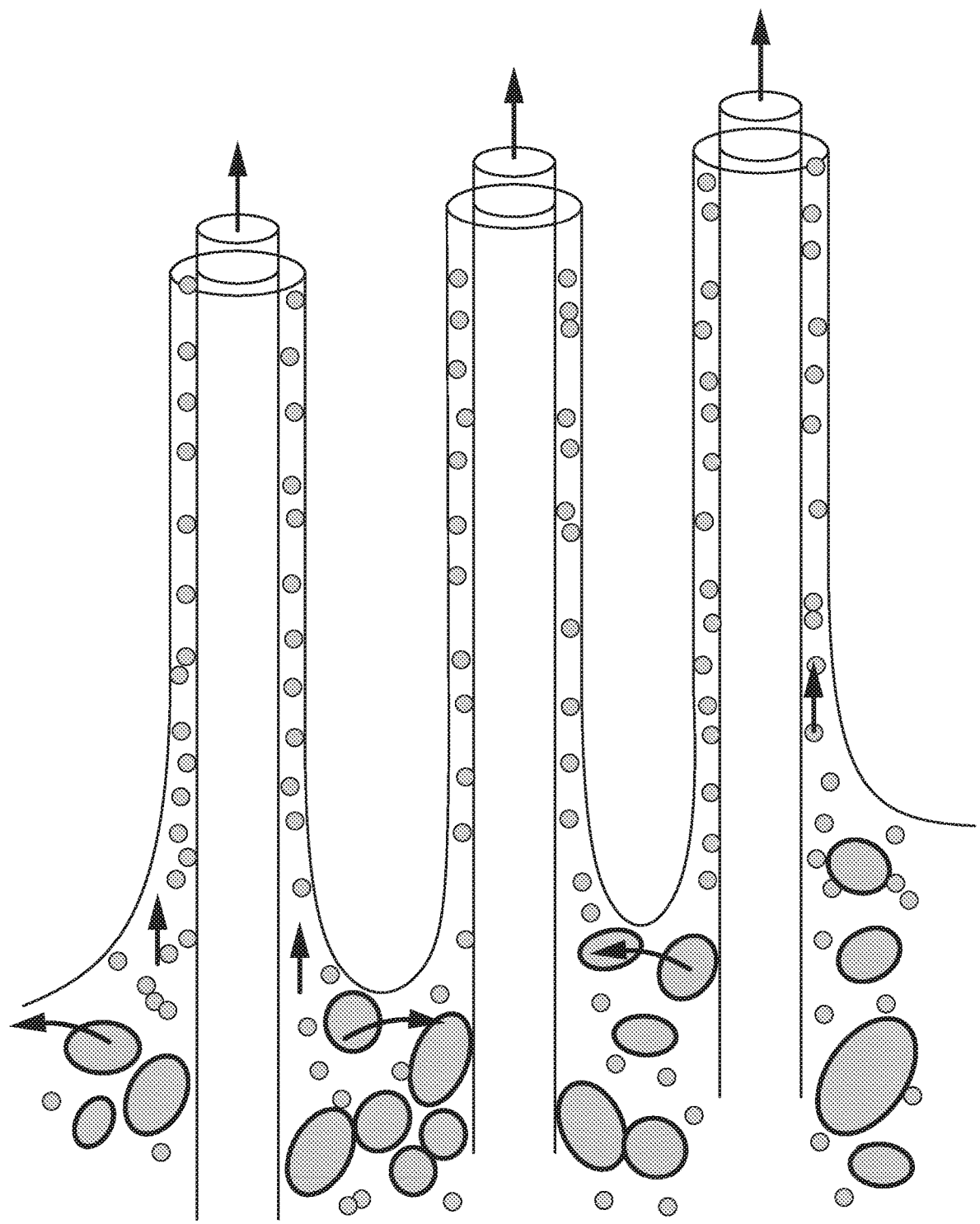
FIG. 4: includes an illustration of an array of wires with separate liquid films on each wire for particle separation according to one embodiment.
Figure 5:
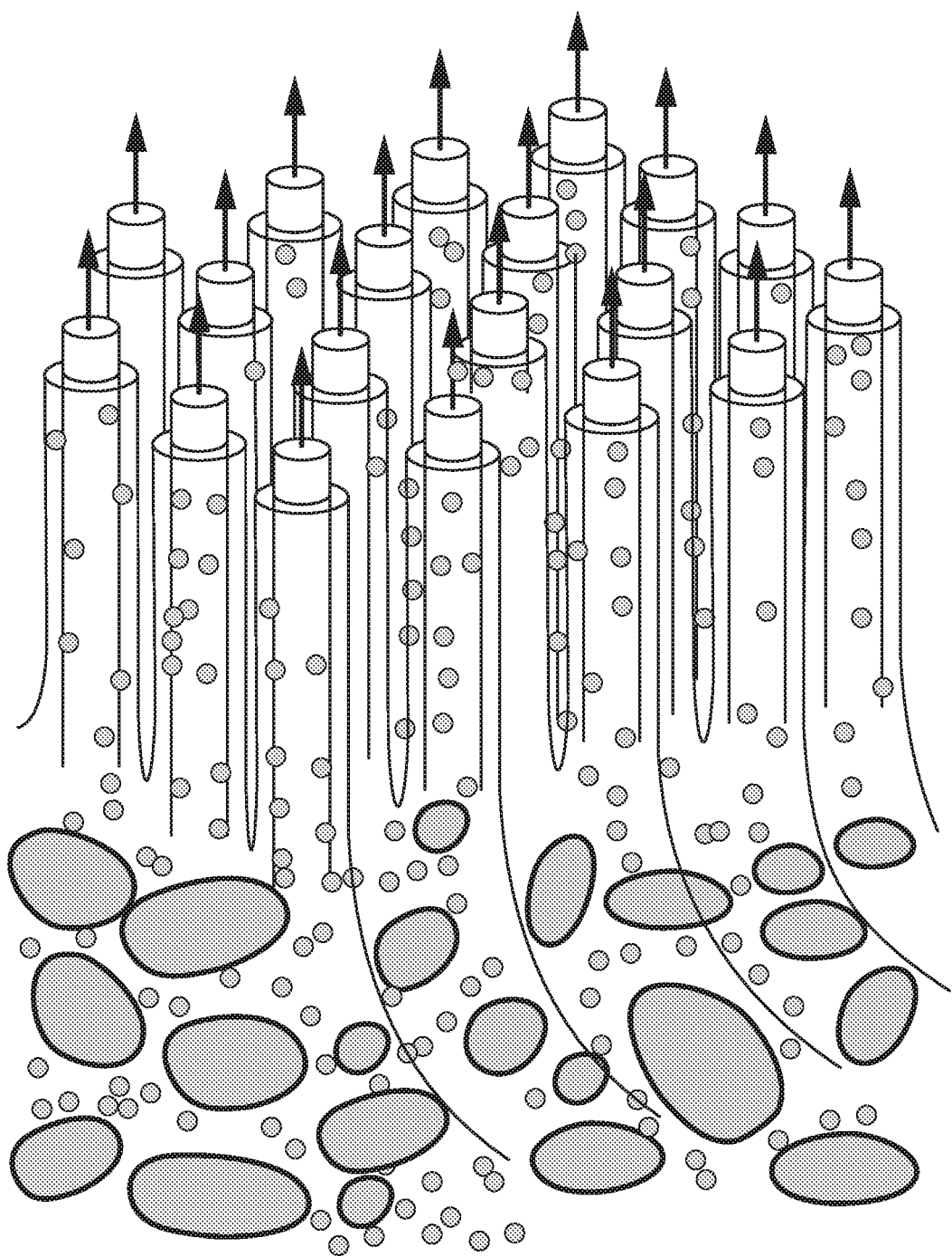
FIG. 5: includes an illustration of an array of wires with separate liquid films on each film for particle separation according to one embodiment.
Figure 6:
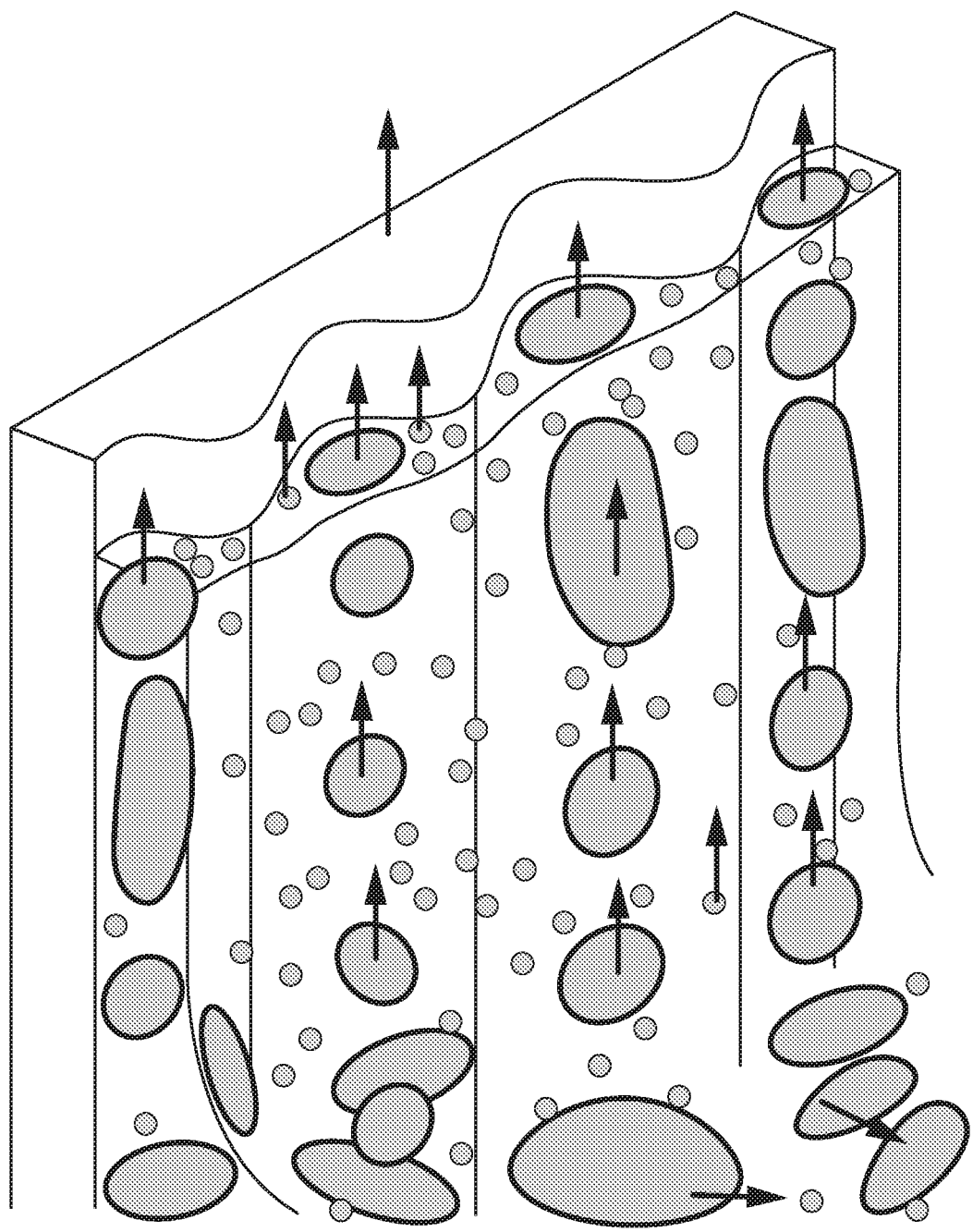
FIG. 6: includes an illustration of a grooved belt including a liquid film for particles separation according to one embodiment.
Figure 7:
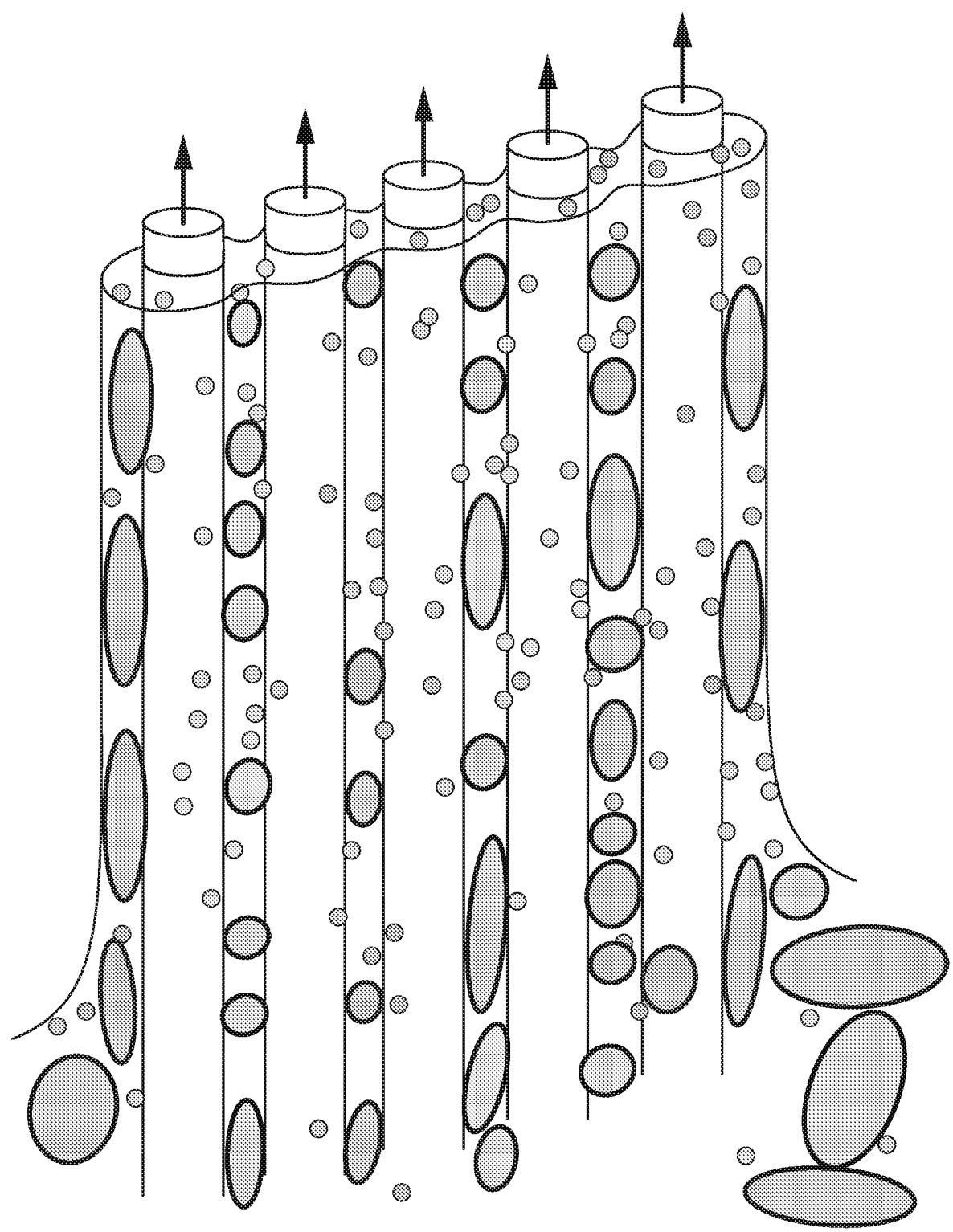
FIG. 7: includes an illustration of an object of closely spaced wires containing liquid bridges according to one embodiment.
Figure 8A:
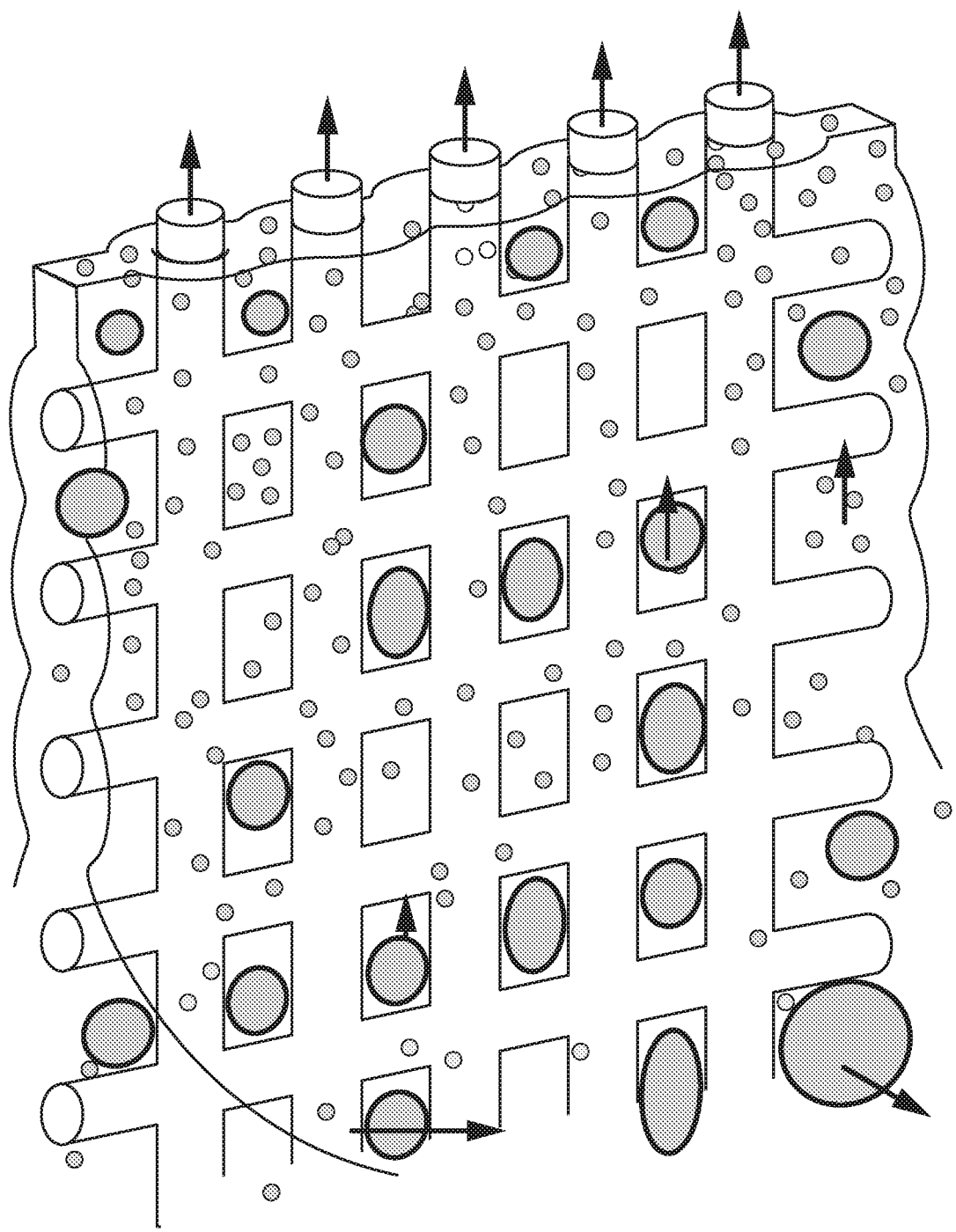
FIG. 8A,B: includes an illustration of a fabric including liquid bridges according to one embodiment.
Figure 8B:
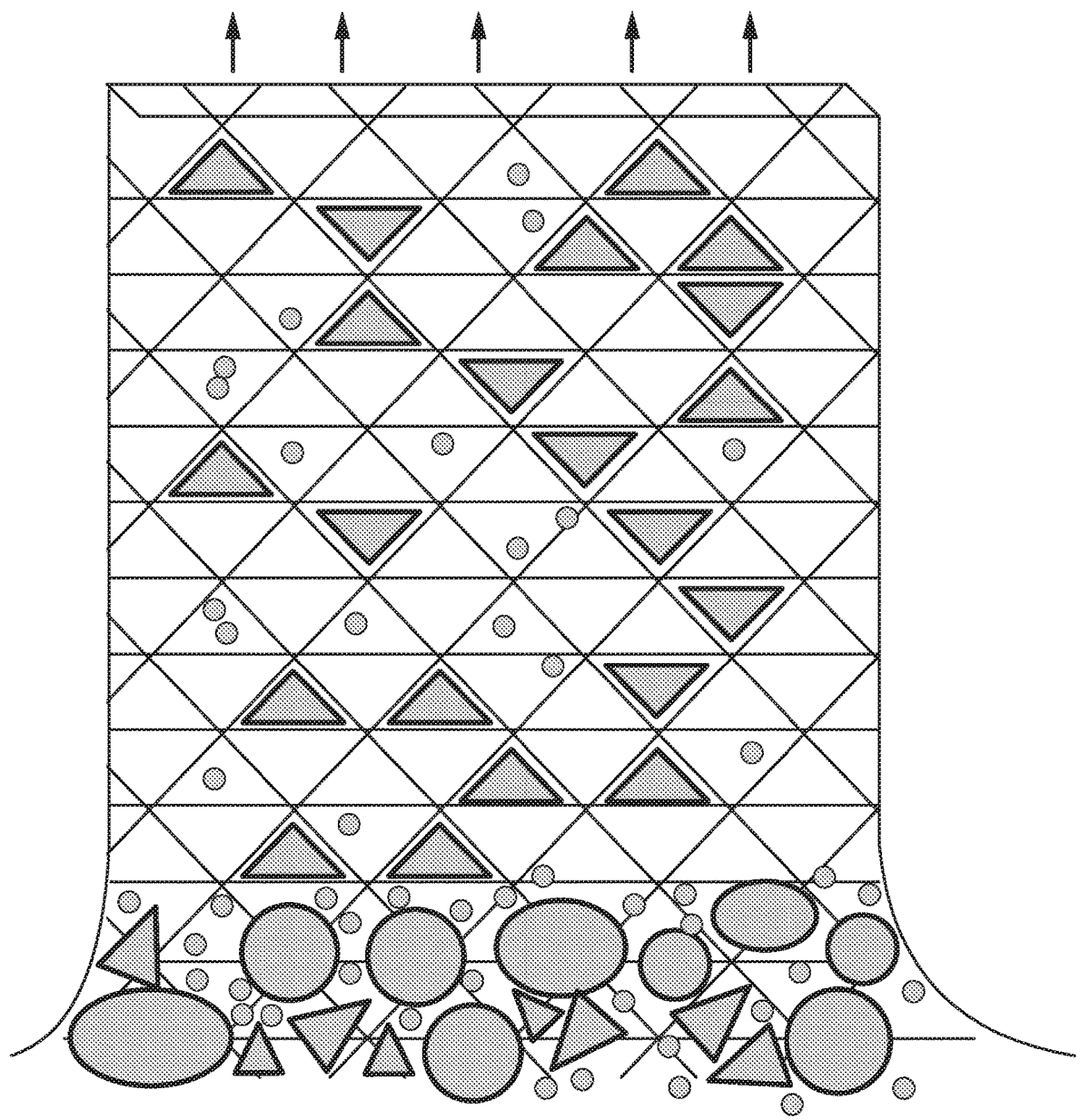

The object used in the process of the present disclosure for removing particles from the dispersion can have a large variety of shapes, dimensions, and chemical composition. In embodiments, the object can be a wire, a sheet, a belt, a woven fabric, or a non-woven fabric. A variety of objects are illustrated in FIGS. 2-8: FIG. 2 illustrates the use of a cylindrical fiber, FIG. 3 illustrates the embodiment of a flat plate, FIGS. 4 and 5 illustrate embodiments of wire arrays with separately liquid films on each wire, FIG. 6 shows a grooved belt that can capture in the grooves larger elongated particles. FIG. 7 illustrates an arrangement of closely spaced wires with liquid bridges formed between the wires liquid. This set up can allow attachment of different types of particles, one type suitable for the bridging regions and another type on the film of the wires. FIG. 8A illustrates the embodiment of a fabric containing liquid bridges, and FIG. 8B illustrates a fabric comprising a patterned structure, such that particles of different shape can be separated from each other within the fabric.

The present disclosure further relates to an assembly for separating particles. The assembly can contain a chamber including a dispersion, the dispersion comprising a liquid and a plurality of particles. The assembly can further contain an object adapted for moving through the dispersion contained in the chamber and adsorbing at least a portion of the plurality of particles during moving. The assembly can further contain a first construction adapted for moving the object relative to the dispersion at a controlled moving speed. By moving the object out of the dispersion, a liquid film can be formed on the surface of the object and particles having a particle size not greater than h* can be removed from the dispersion with the liquid film. In a further aspect, the assembly can contain a second construction adapted for removing and collecting from the object a plurality of separated particles from the dispersion.

Figure 9:
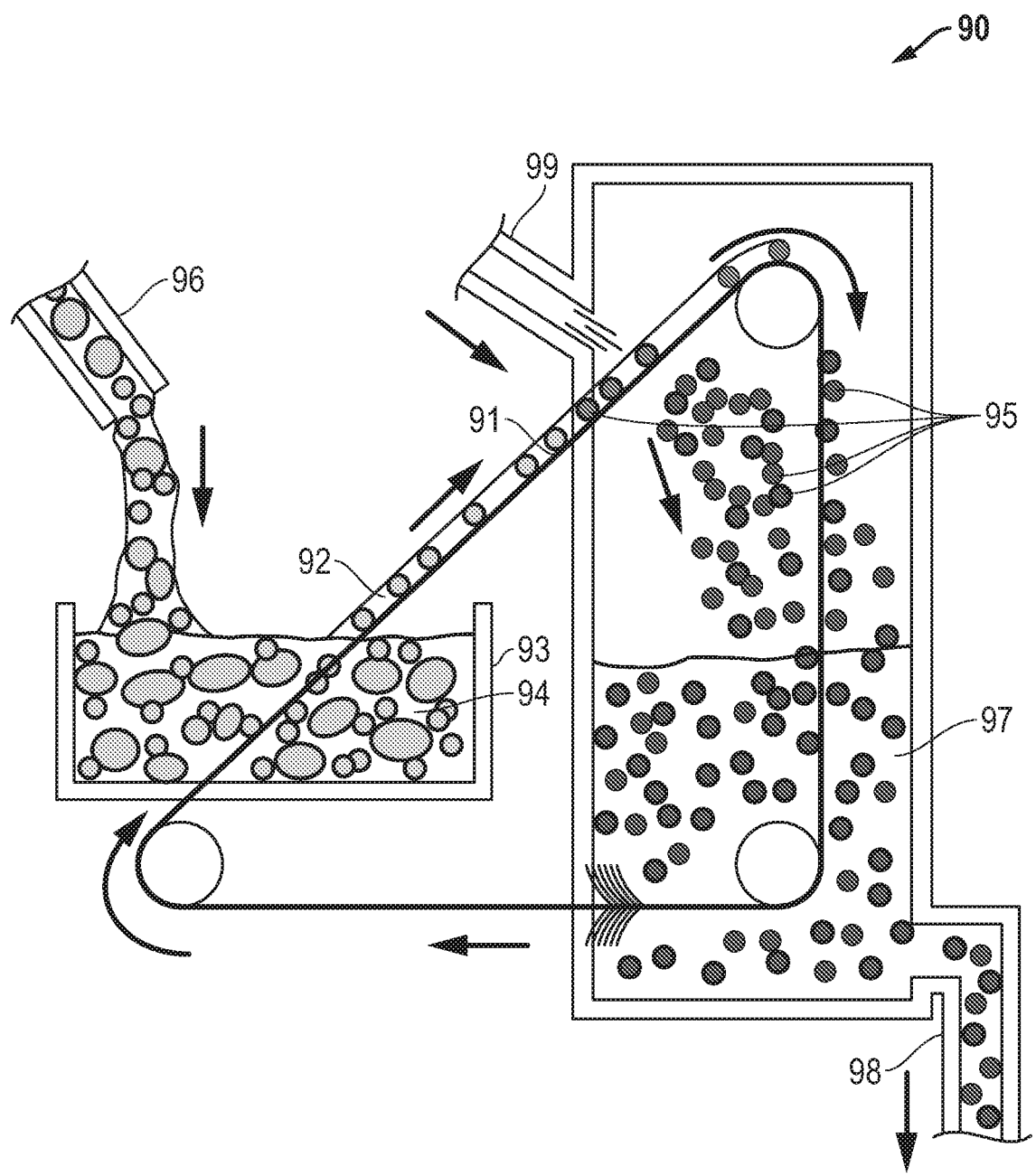
FIG. 9 includes an illustration of a continuous filtering process according to one embodiment.

Non-limiting examples of a assemblies are illustrated in the embodiments of FIGS. 9-14:

FIG. 9 includes an illustration of an embodiment of a continuously operating assembly (90) including as object a belt (91) moving through a chamber (93) including a liquid dispersion (94) containing a plurality of particles. A liquid film (92) can be formed on the belt (91) when leaving the dispersion (94) which can include particles (95) separated from the dispersion (94) The chamber (93) can include an inlet (96) for continuously providing the dispersion (94). The separated particles (95) contained in the liquid film (92) on the moving belt can be sprayed off from the belt with a liquid (e.g., liquid jet or spray) (99) and collected in a collection tank (97), which can include an outlet (98). The belt can be cleaned with a brush when leaving the collection tank (97) and be returned to the chamber (93) containing the particle dispersion (94).

Figure 10A:
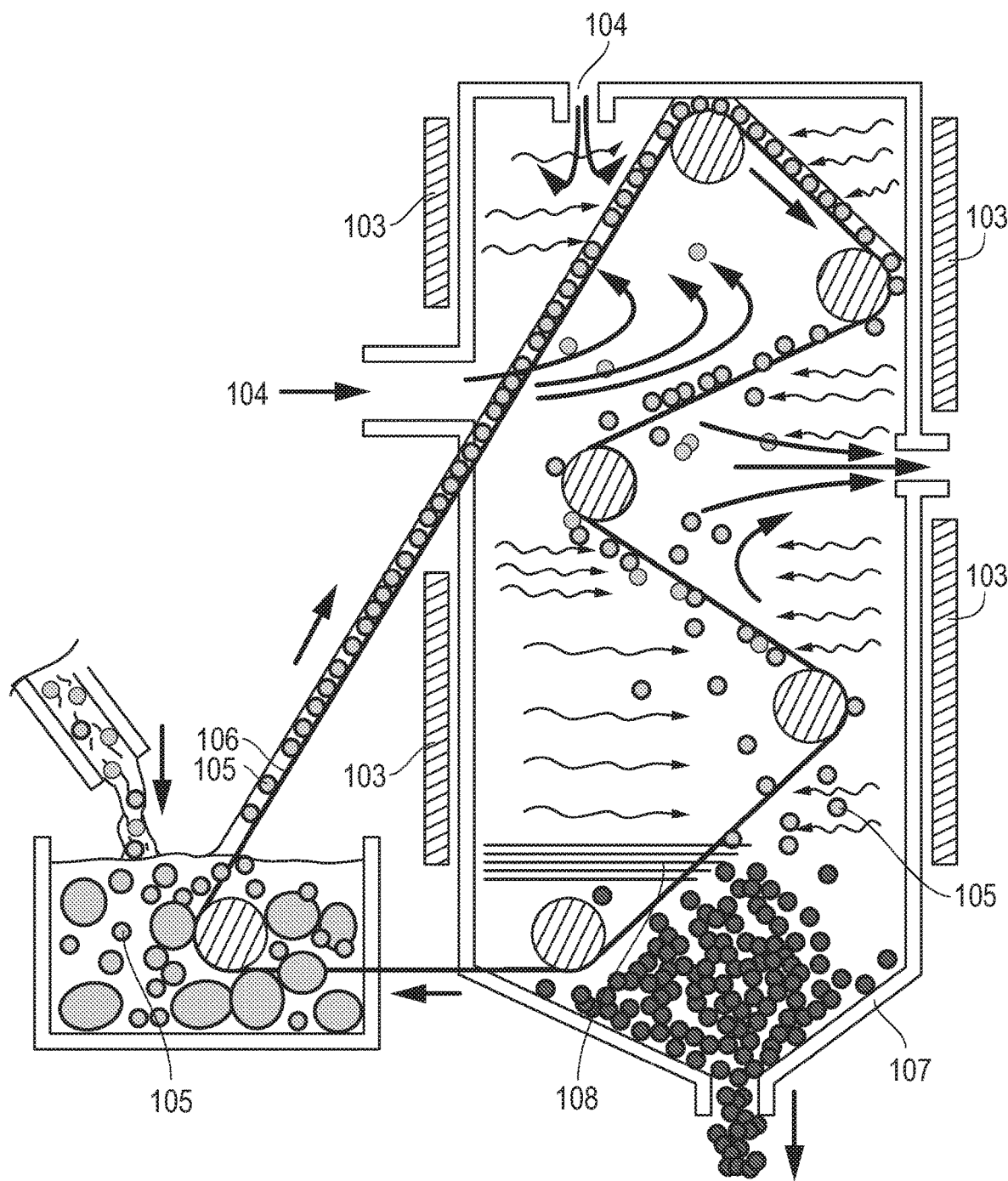
FIG. 10A: includes an illustration of a continuous filtering process according to one embodiment.
Figure 10B:
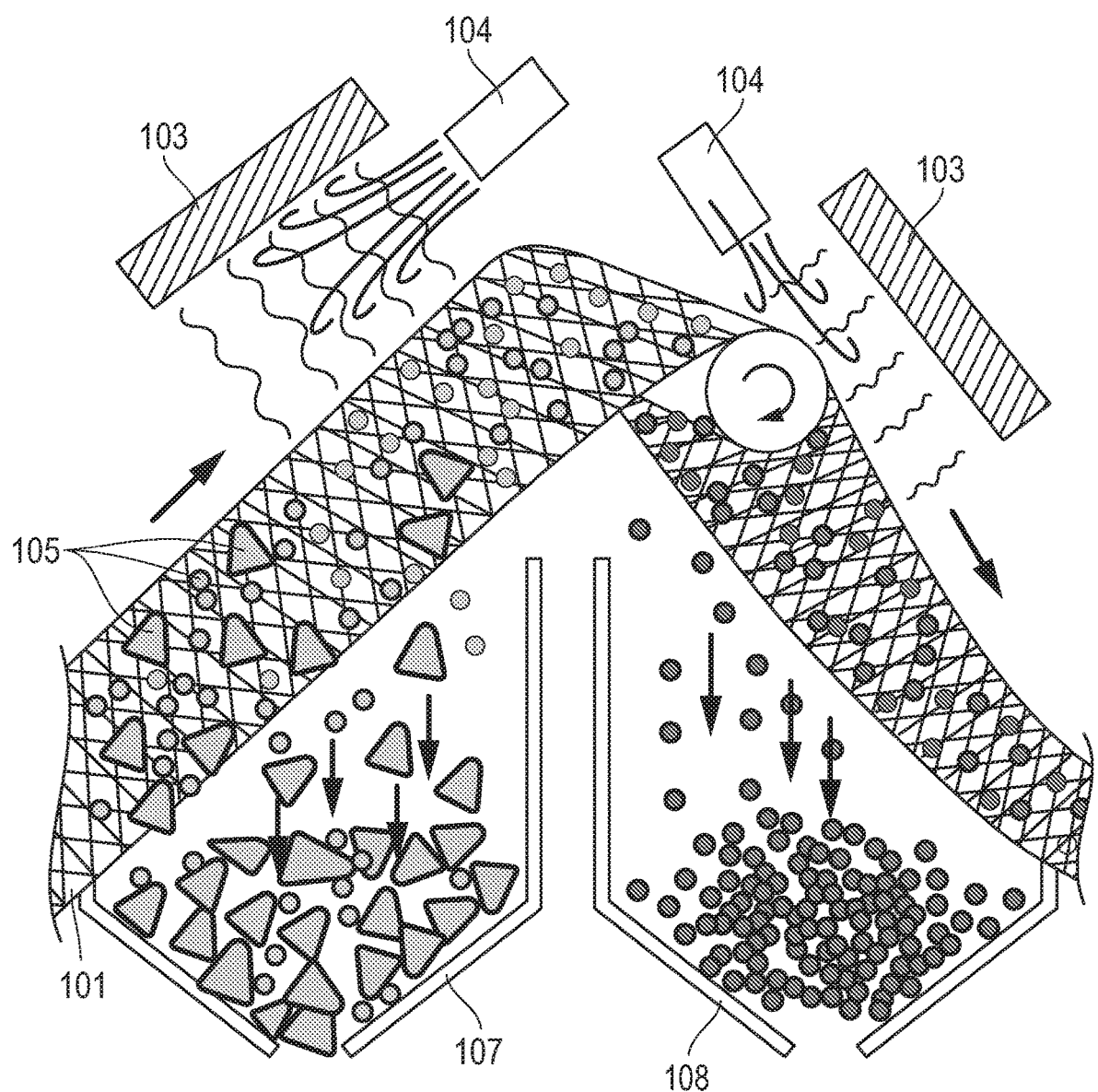
FIG. 10B: includes an illustration of a continuous filtering process according to one embodiment.
Figure 10C:
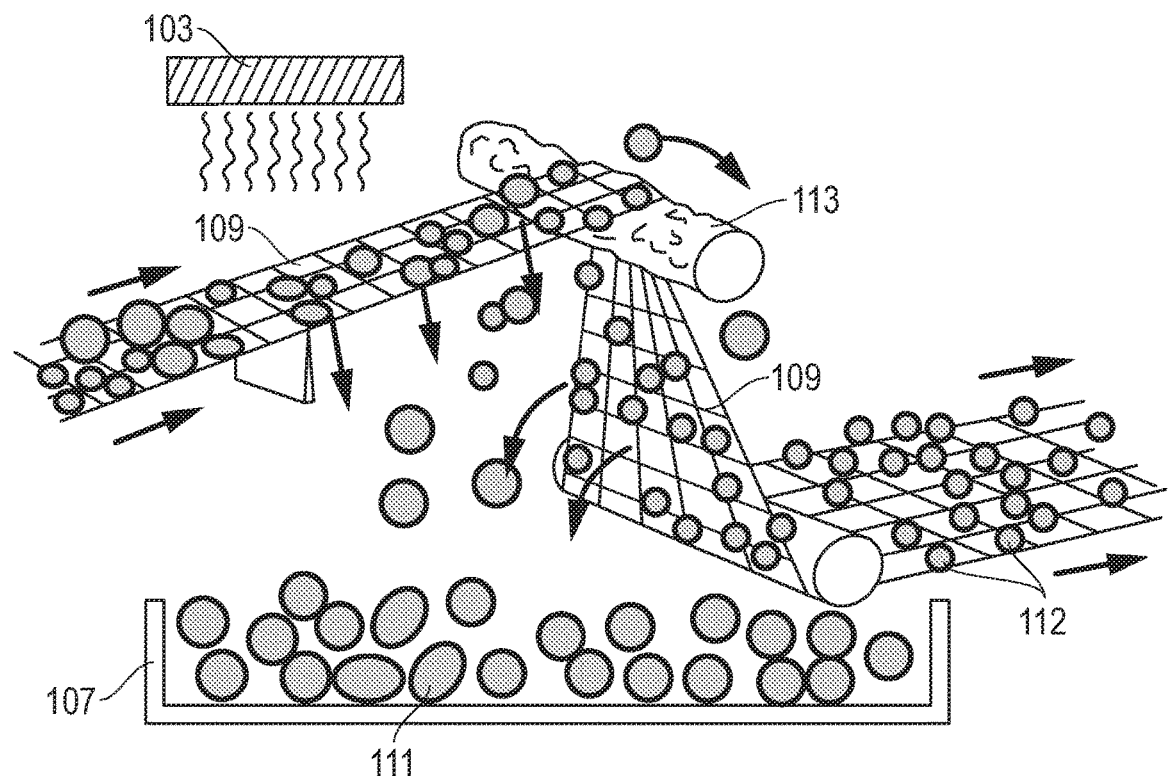
FIG. 10C: includes an illustration of a continuous filtering process according to one embodiment.
Figure 10C:
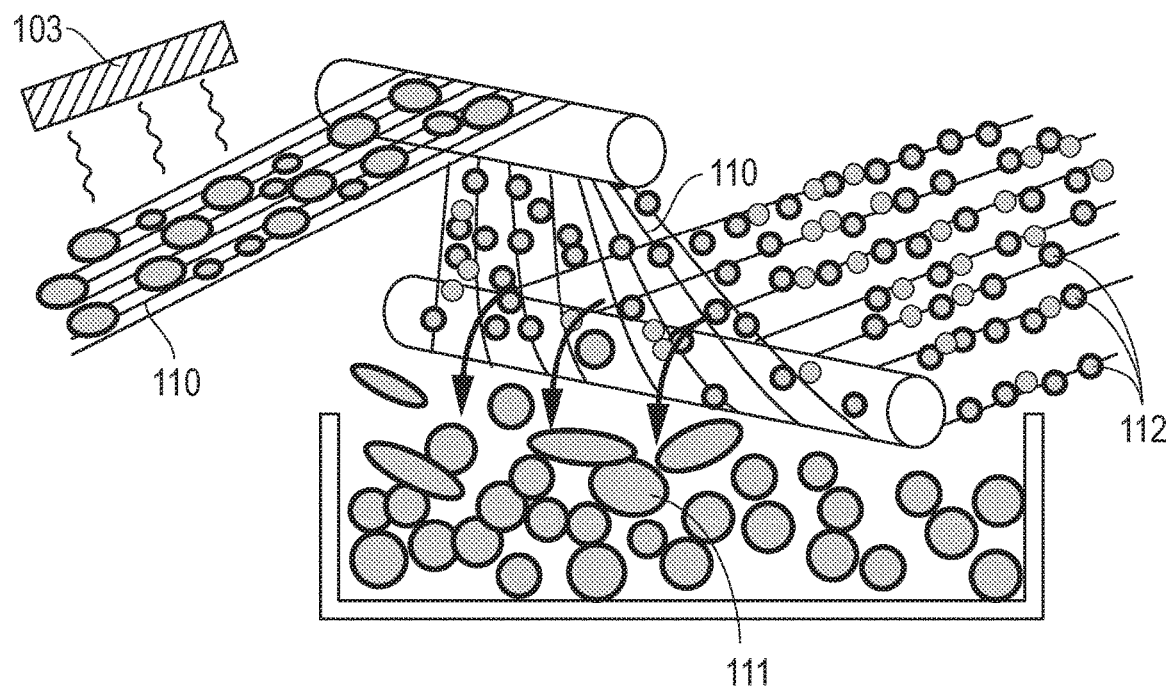

FIGS. 10A, 10B and 10C illustrate embodiments wherein the liquid film 102 on the object (106) can be dried with a heater (103) and evaporated with warm air (104). After evaporation of the liquid and drying of the separated particles (105), the dried particles can fall off from the belt, fabric or wire in a collection tank (107). In addition, the dried separated particles can be brushed off from the belt with a brush or knife (108). FIG. 10B illustrates an embodiment wherein a fabric (101) loaded with a liquid film including separated particles (105) after capillary filtering is moved to a heating area containing heaters (103) and blowers of warm air (104), and larger shaped particles can be dried and fall into a first collection tank (107) and remaining smaller particles can be dried in a second drying region and fall into a second collection tank (108). The embodiments shown in FIG. 10C illustrate the drying and separation of particles with different size after capillary filtering via a stretchable fabic (109) or a plurality of closely spaced wires (110). By stretching the fabric (109) or widening the spaces between the wires (110), the larger sized separated particles (111), can fall in a first collection tank (107), while the smaller particles (112) can remain on the fabric or wire and collected at a later unit (not shown) by appropriate treatment.

Figure 12:
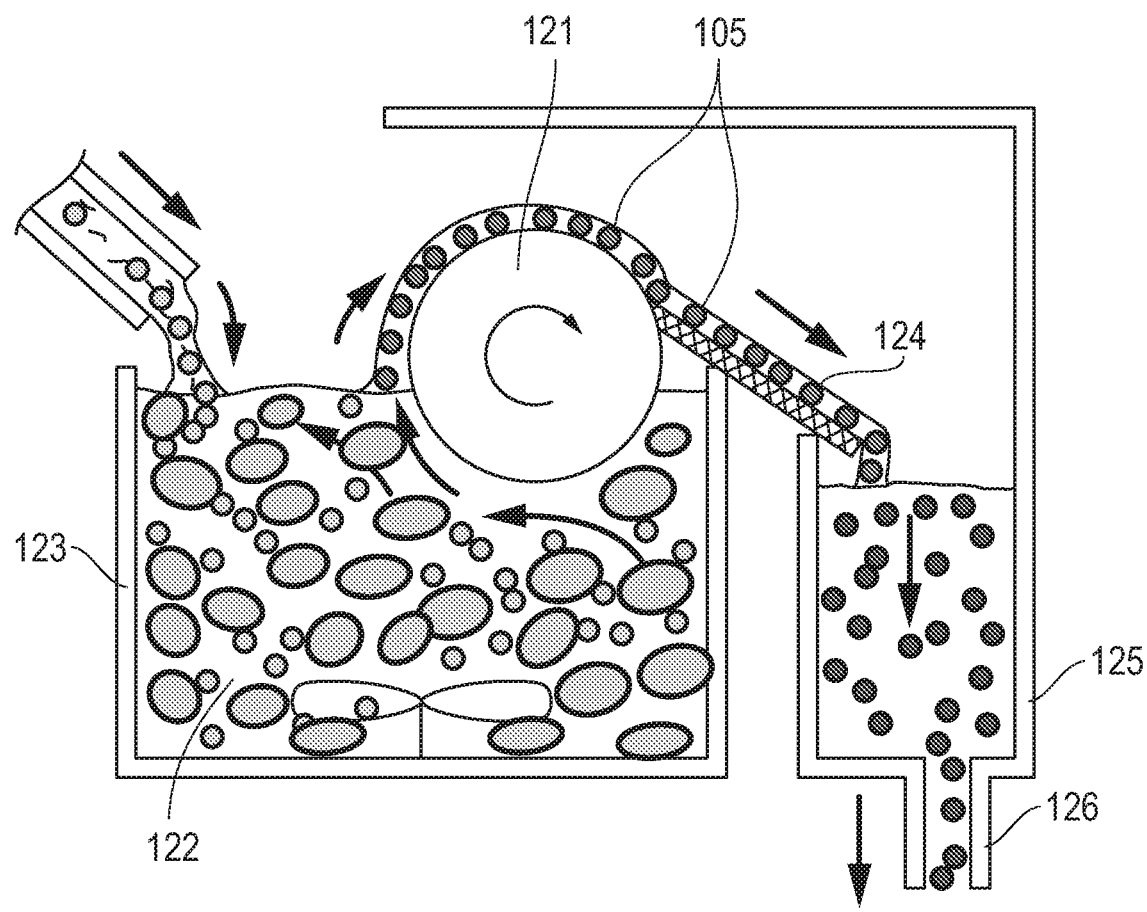
FIG. 12: includes an illustration of a continuous filtering process according to one embodiment.

Another embodiment of a continuous process is illustrated in FIG. 12. A rotating roller (121) can rotate through a dispersion (122) of a chamber (123). The rotating roller can create a meniscus for achieving a desired particle separation, and the separated particles (105) can be removed with a knife (124) from the roller (121) and guided to a collection tank (125) having an outlet (126). In certain aspects, the roller (121) can contain grooves, bumps, or cavities to capture particles of different sizes and/or shapes.

Figure 13:
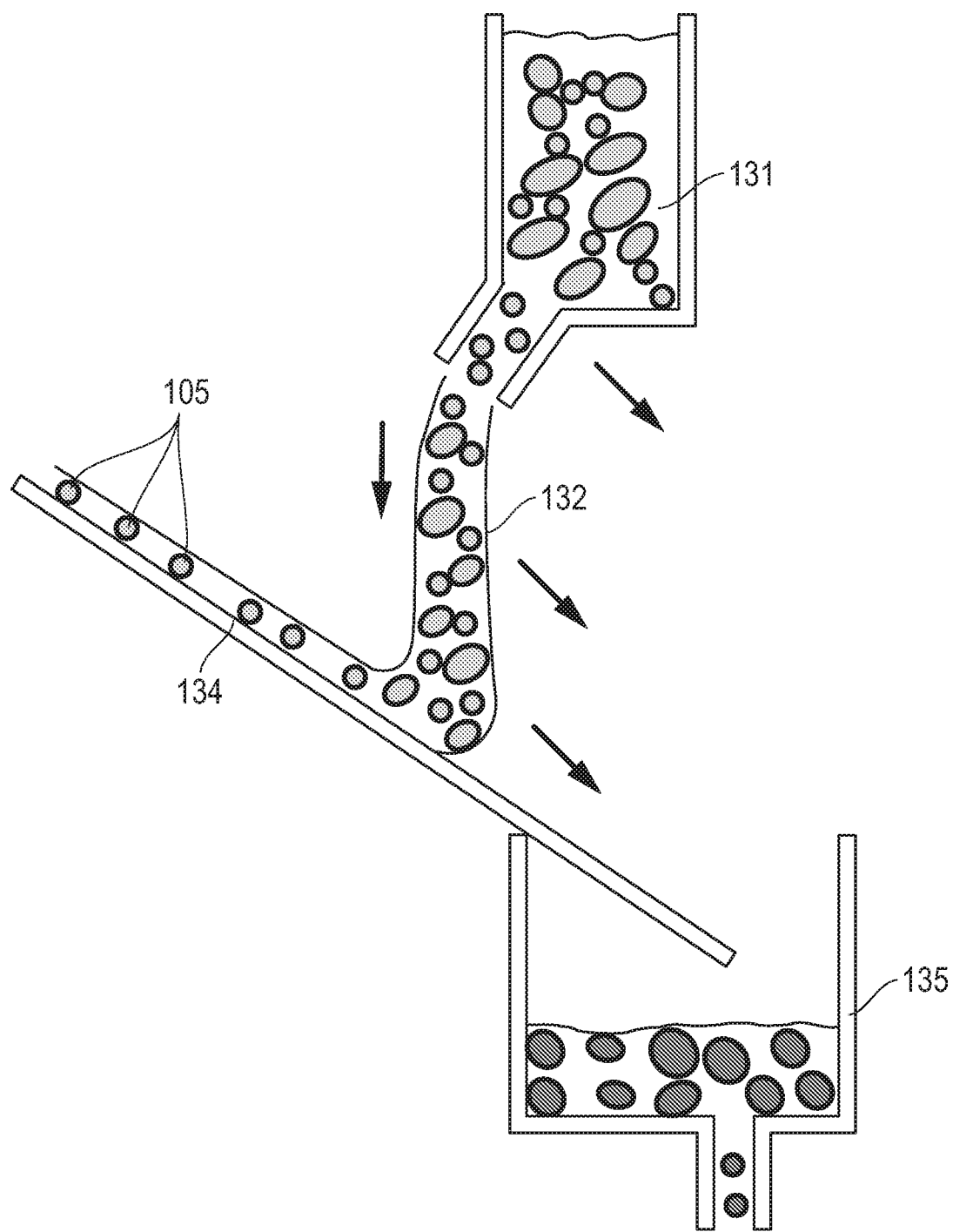
FIG. 13: includes an illustration of a continuous filtering process according to one embodiment.
Figure 14:
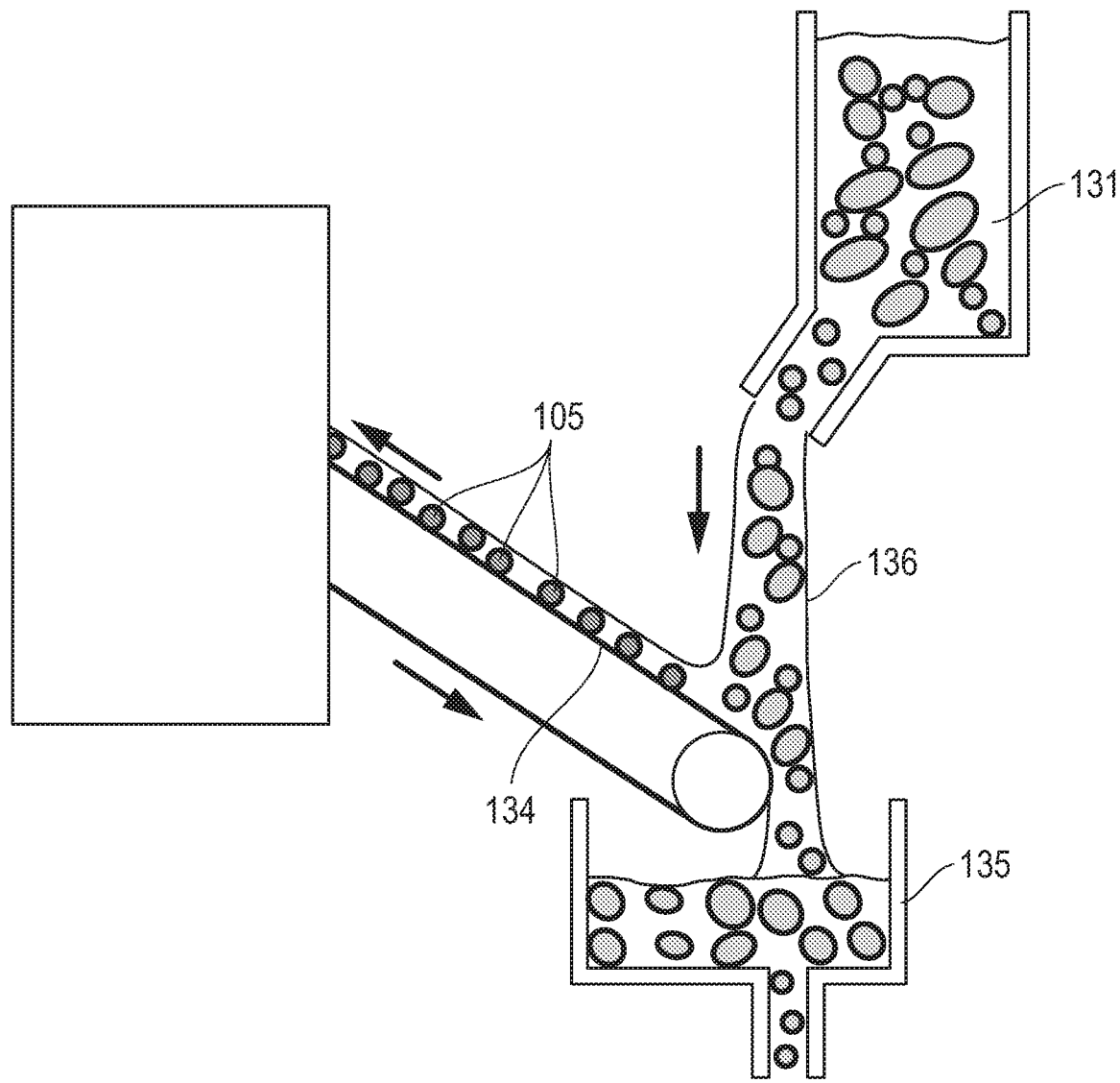
FIG. 14: includes an illustration of a continuous filtering process according to one embodiment.

FIG. 13 illustrates an embodiment of a continuous filtering process setup wherein the dispersion (131) can be guided as a free-standing liquid curtain (132) to flow on a moving sheet (134) and separated particles may be collected in a collection tank (not shown), while the other part of the dispersion can flow in an outlet tank (135). FIG. 14 illustrates an embodiment wherein the dispersion can have the function of a fixed curtain (136).

Figure 11:
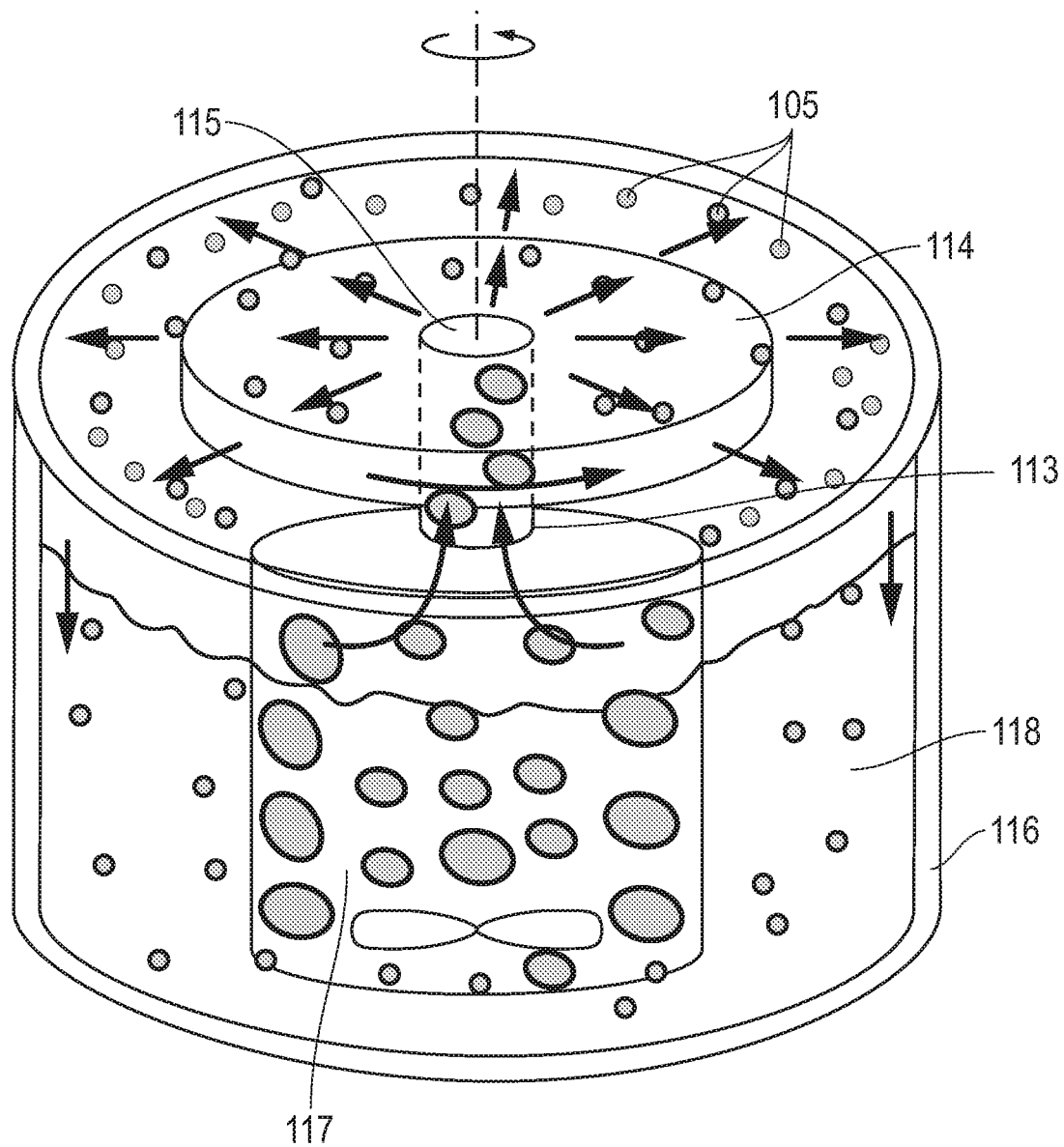
FIG. 11: includes an illustration of a filtering process according to one embodiment.

Another embodiment of a filtering process can be based on the principle of spin coating, as illustrated in FIG. 11. In this embodiment, the input dispersion (117) may be introduced through a pipe (113) from below a spinning disk (114) with a central orifice (115). The filtration occurs as the dispersion is pushed into the spin coating by inertial forces, opposed by capillary forces in the meniscus, which can prevent particles from entering whose smallest diameter is larger than the stagnation point. In one embodiment, the separated particles (105) in the spin coating may be ejected from the spinning disk into a concentric collection tank (116), wherein the particles can either fall directly into a collection liquid (118) or can hit the outer walls and drip downward for collection. In aspects, the disk surface may be smooth or patterned. The radial profile of the disk may be flat and perpendicular to the axis of rotation, as shown. Alternatively, to take advantage of different flow profiles, the surface may be curved like a convex bowl, or shaped like a cone.

The present disclosure further employs theoretical calculations which can simulate and predict process parameters for controlling a desired particle fraction attached to the moving object during filtration. Embodiments of the calculations may be based on the following equations (1) to (6):

Equation (1) expresses the Colosqui-Morris-Stone criterion that the diameter d of the particles captured in the film attached to the moving object may be smaller than a critical value d* equal to the thickness of the dynamic meniscus at the stagnation point h* of the liquid flow, which separates streamlines entering the liquid film from those returning to the liquid reservoir (as also illustrated in FIG. 1):

$$d < d^* = h^* \quad (1)$$

The relative effect of viscous stresses to surface stresses in the meniscus region during capillary filtration can be expressed by the capillary number Ca, $$Ca = \frac{U\mu}{\gamma} = \frac{U}{U_c} \quad (2)$$

wherein $\mu$ is the viscosity of the fluid, $\gamma$ is the surface tension of the fluid, U is the velocity of the fluid during pulling the object out of the fluid (also called herein solid surface velocity of the moving object or pull rate); and $U_c$ is the capillary speed ($\gamma/\mu$).

The limiting film thickness is given by Equation (3), the Landau-Levich-Deryaguin formula, which was developed for the coating of flat sheets and is valid for Ca☐1.

$$h_f = \alpha \ell \, Ca^{2/3} \quad (3)$$

In the present disclosure, it is assumed for a flat sheet that $\alpha = 0.95$ and $$\ell = \ell_c = \sqrt{\frac{\gamma}{\rho g}},$$

wherein $l_c$ is the capillary length, $\gamma$ the viscosity of the liquid, g the gravitational constant and $\rho$ the density of the dispersion, including the suspended particles. In the embodiment that a cylinder having a radius much smaller than the capillary length R☐$l_c$ is used, i.e. the limit of small Bond number Bo=$(R/\ell_c)^2 \ll 1$, it is assumed that $\ell = R$, and $\alpha = 1.34$.

For the embodiment of having a small capillary number with Ca below 0.1, the following scaling relation shown of equation (4) can be postulated, $$d^* = \beta h_f \quad (4)$$

wherein $\beta = 3$ for a flat plate and $\beta = \frac{3}{2}$ for a cylinder of radius much smaller than the capillary length.

The calculation of a required moving speed U of the object when pulling it out of the dispersion (herein also called the solid substrate velocity U) in relation to a desired particle size cutoff can be derived by combining equations (3) and (4) to equation (5).

$$U^* = U_c \cdot \left( \frac{d^*}{\alpha \beta \ell} \right)^{3/2} \quad (5)$$

Based on equation (5), simulations of the critical pulling speed U* corresponding to a desired particle size cutoff can be calculated.

The critical flow rate of a liquid dispersion removed by the object during the filtration can be calculated according to equation (6), derived from the previous equations. As used herein, the critical flow rate is also called fluid removal rate at a given particle size cutoff.

$$Q_f^* = PU^* h_f = \frac{PU_c}{(\alpha \ell)^{3/2}} \left( \frac{d^*}{\beta} \right)^{5/2} \quad (6)$$

where P is the total perimeter of the liquid film, given by P=$2\pi R N_w$ for $N_w$ the amount of wires of radius R, and P=2 W for a flat sheet of width W coated on both sides.

The filtering process of the present disclosure may be more efficient with decreasing capillary number Ca. In one embodiment, decreasing the capillary number Ca can be achieved by maximizing the capillary speed Uc, for which a liquid can be selected having a low viscosity and and a high surface tension. In this regard, water can have an advantage compared to other liquids. Water has a capillary speed of 81 m/s at 25° C., which is larger than for most other liquids, due to its high surface tension and relatively low viscosity. As shown in Tables 1 and 2 of the examples, other representative organic liquids, such as acetone, toluene, or hexane, have smaller capillary speeds, despite having lower viscosities, due to their significantly lower surface tension in comparison to water.

In a particular aspect, using warm liquids can increase the efficiency of the filtering process. As also shown in the examples, the capillary speed of water more than doubles if the temperature is increased from 25° C. to 90° C., since the viscosity of water lowers to a larger extent than its surface tension increases with increasing temperature. Evaporation of warm water can be also more efficient during dry extraction of the particles from the surface of the object after capillary filtration.

In one aspect, it may be desirable to lower the efficiency of capillary filtering by selecting a liquid with low surface tension and thereby decreasing the capillary speed, to take advantage of a low boiling point and increased volatility for more efficient evaporation and dry particle extraction. In this regard, the costs of heating the initial dispersion may need to be compared with reduced costs of separation.

Figure 15:
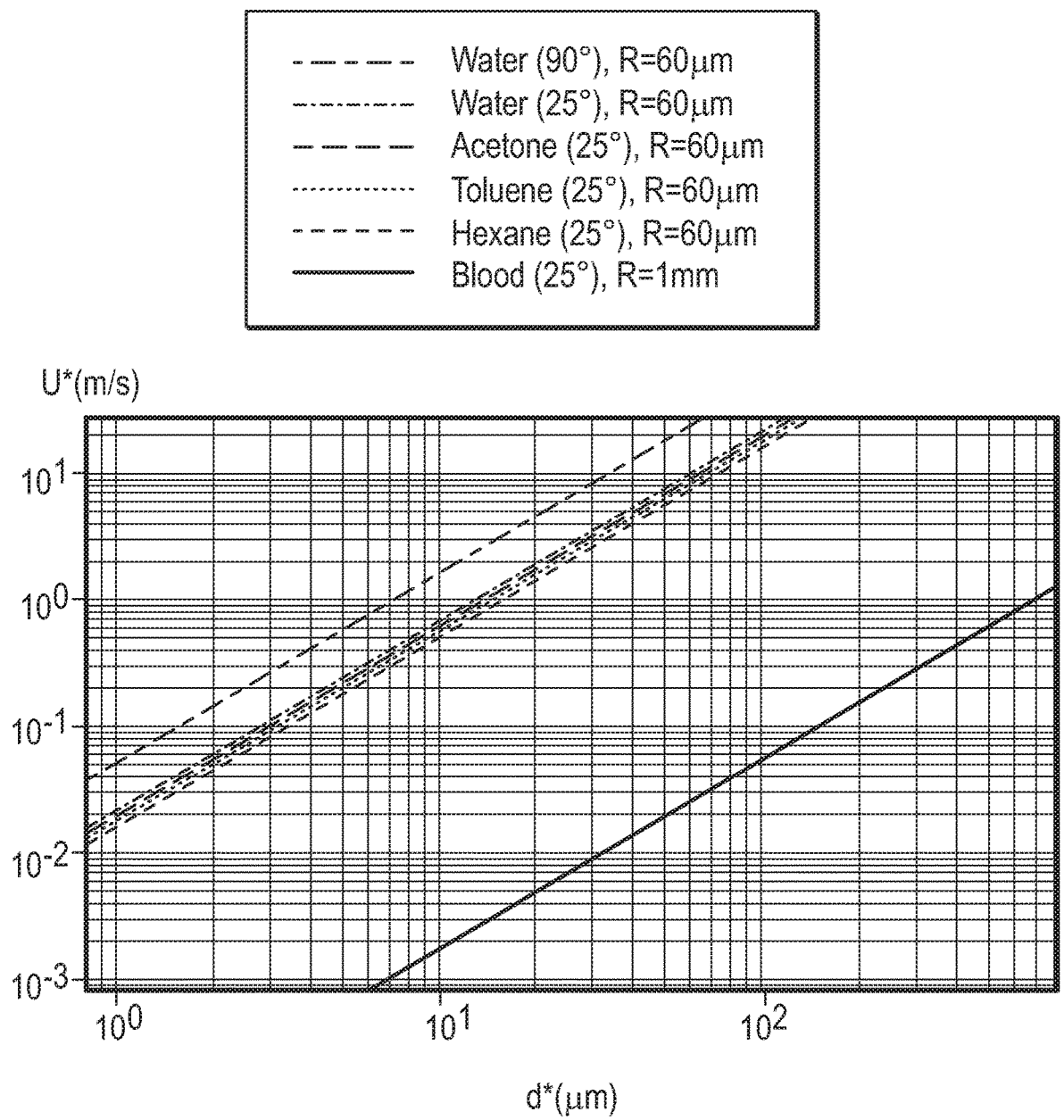
FIG. 15: includes a graph demonstrating a relationship of moving speed vs. cutoff size according to one embodiment.

In one embodiment, equation (5) can be used for simulating particle separation of moving objects and calculating a required maximum pulling speed (also called herein critical pulling speed) for separating particles with a desired particle size (also called herein particle cutoff size) when moving an object out of a a particle dispersion. FIG. 15 illustrates simulations of particle separation according to embodiments by using a cylinder as moving object with a of radius R=$\ell$=60 µm, and several representative liquids having a high capillary speed, such as water, acetone, toluene, benzene. It can be seen that warm water may be particularly effective to reach a high pulling speed for separating particles of a particle size range between about 1 to 100 microns. Using wires with a radius of 60 μm, the critical pulling speed can vary from 10 cm/s to 10 m/s, with a corresponding particle diameter cutoff ranging from 2 μm to 60 μm in water at 25° C., or from 0.5 μm to 22 μm in water at 90° C.

In another embodiment, more viscous liquids having a smaller capillary speed may produce thicker coatings, and therefore can require a lower moving speed than dispersions including liquids of lower viscosity to achieve the same particle size cutoff. In the case of whole blood, the pulling speed may need to come down to below 1 mm/second in order to achieve separation of blood constituents in a range below 10 microns, as shown in FIG. 15 for a wire having a radius of 1 mm. Accordingly, for a whole blood sample, a larger wire radius was selected to reduce the shear strain rate for cell viability, as also demonstrated in Example 6.

Figure 16:
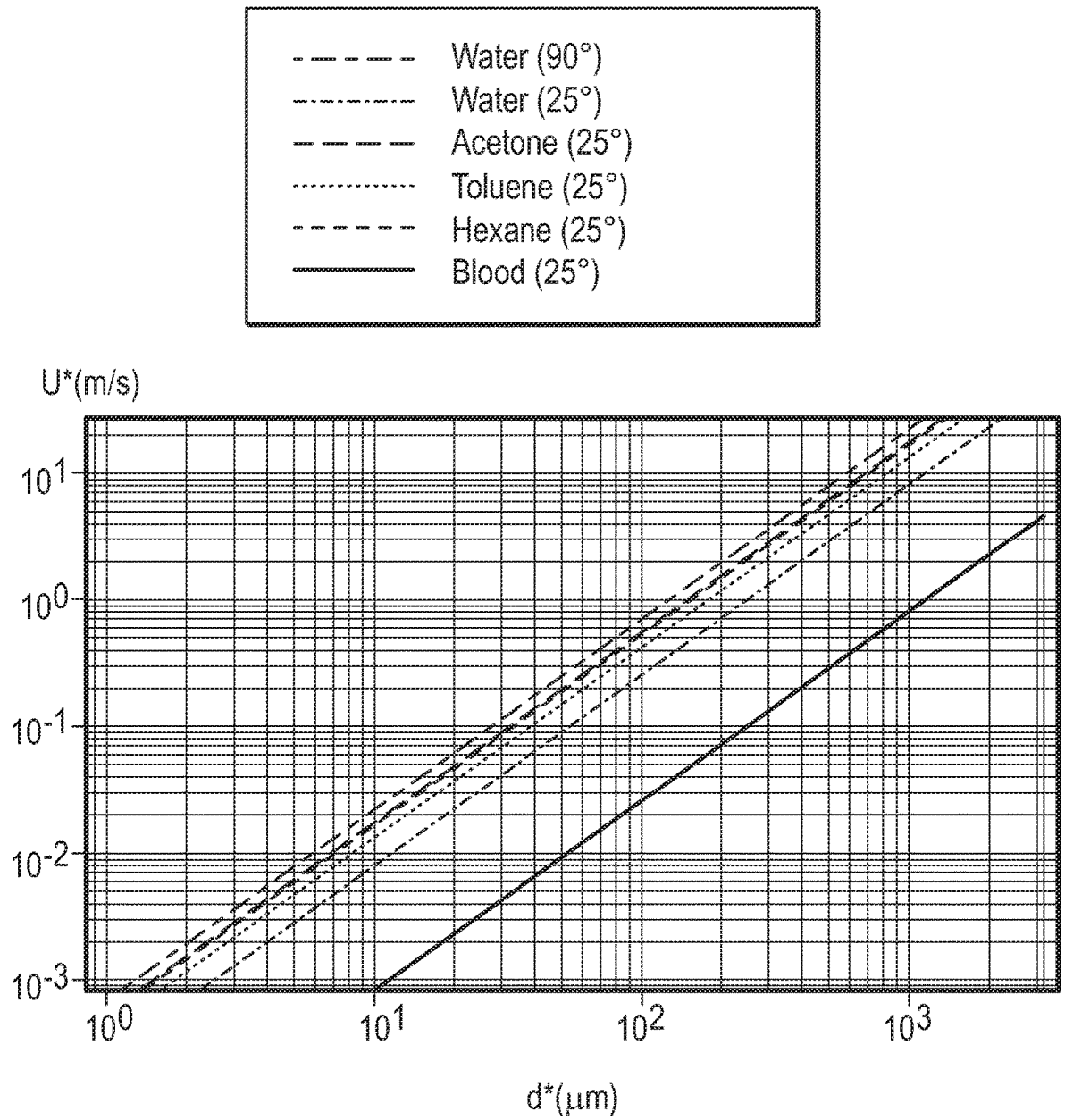
FIG. 16: includes a graph demonstrating a relationship of moving speed vs. cutoff size according to one embodiment.

The relationship of critical pulling speed versus cutoff size for a flat sheet according to equation (5) is illustrated in FIG. 16, using the same type of fluids as in FIG. 15. In the case of vertically pulling a flat sheet from a dispersion, it was assumed that $\ell = \ell_c$ (capillary length). Compared to the embodiments of FIG. 15, which employ as moving objects thin wires, FIG. 16 illustrates that much lower pulling speeds may be required to achieve the same particle cutoff diameter, due to the thicker film on the vertical flat sheet compared to a thin wire.

Figure 17:
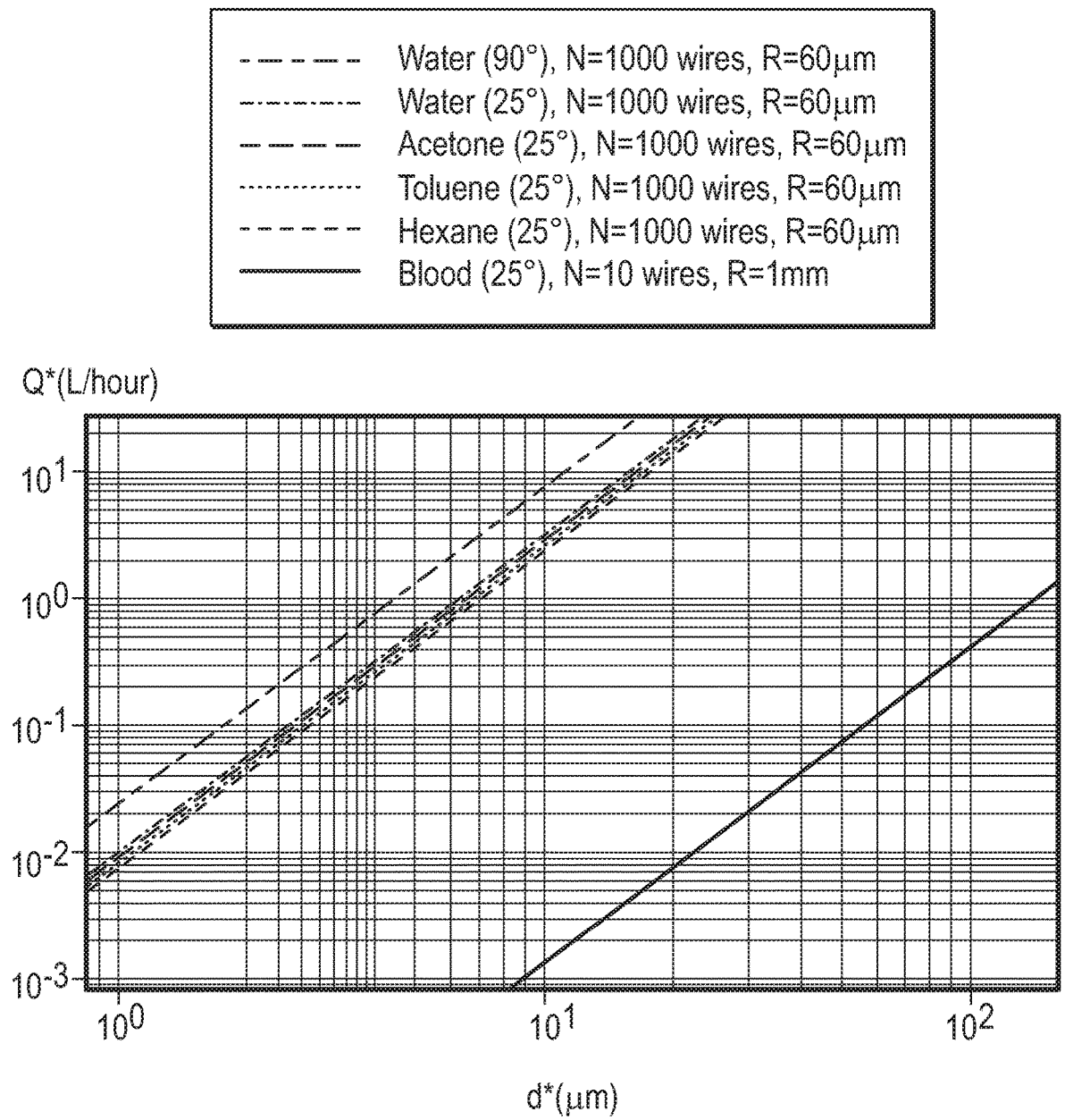
FIG. 17: includes a graph demonstrating a relationship of flow rate vs. cutoff size according to one embodiment.

The critical flow rate for given cutoff size, also called herein fluid removal rate, of the filtering process of the present disclosure can be calculated according to equation (6). In one embodiment, for capillary filtering using as object a plurality of wires, wherein the amount of wires can be $N_w = 1000$, and each wire can have a radius R=60 μm, the critical flow rates of particles dispersed in water, acetone, toluene, and hexane may be deducted from the graph shown in FIG. 17. For water at room temperature, the critical fluid removal rate $Q^*_f$ can vary from 0.1 L/h to 100 L/h with a corresponding cutoff size from 1.5 μm to 60 μm. Acetone, toluene, and hexane have comparable but slightly lower flow rates than water. For warm water at 90° C., the critical flow rate can be about 2.5 times larger for the same particle cutoff size d*.

Figure 18:
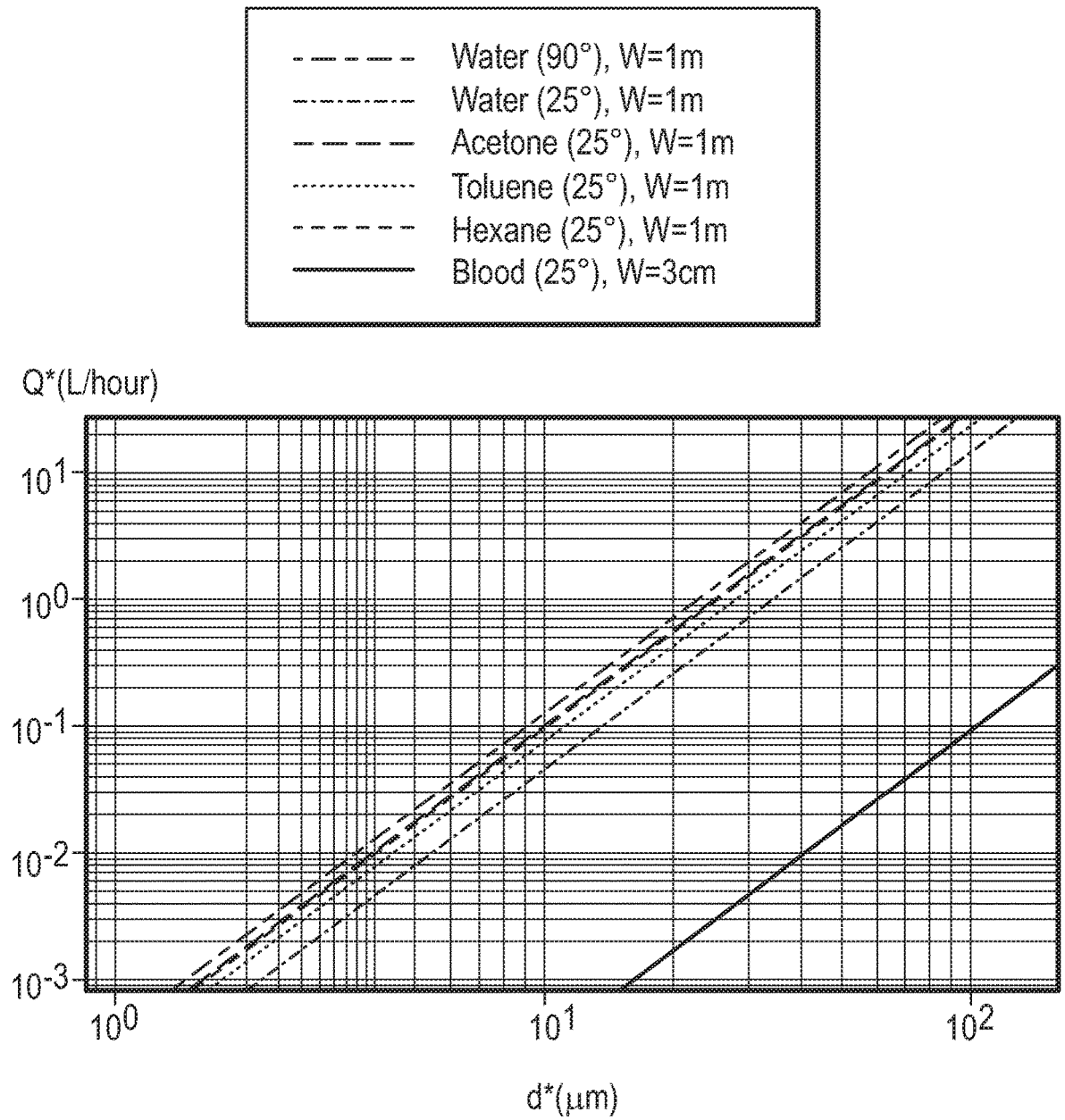
FIG. 18: includes a graph demonstrating a relationship of flow rate vs. cutoff size according to one embodiment.

In another embodiment, when using a flat sheet of 1 meter width as moving object for conducting the filtering process of the present disclosure, the critical flow rate in relationship to the particle cutoff size can behave as illustrated in FIG. 18. It can be seen that warm water has the highest flow rate for a given cutoff size, followed closely by acetone, toluene, and hexane at 25° C. The difference between water at 90° C. and at 25° C. can be explained by the different capillary lengths. In comparison to the plurality of wires discussed above, the critical flow rate of the sheet can be much lower by an order of a magnitude.

Figure 20:
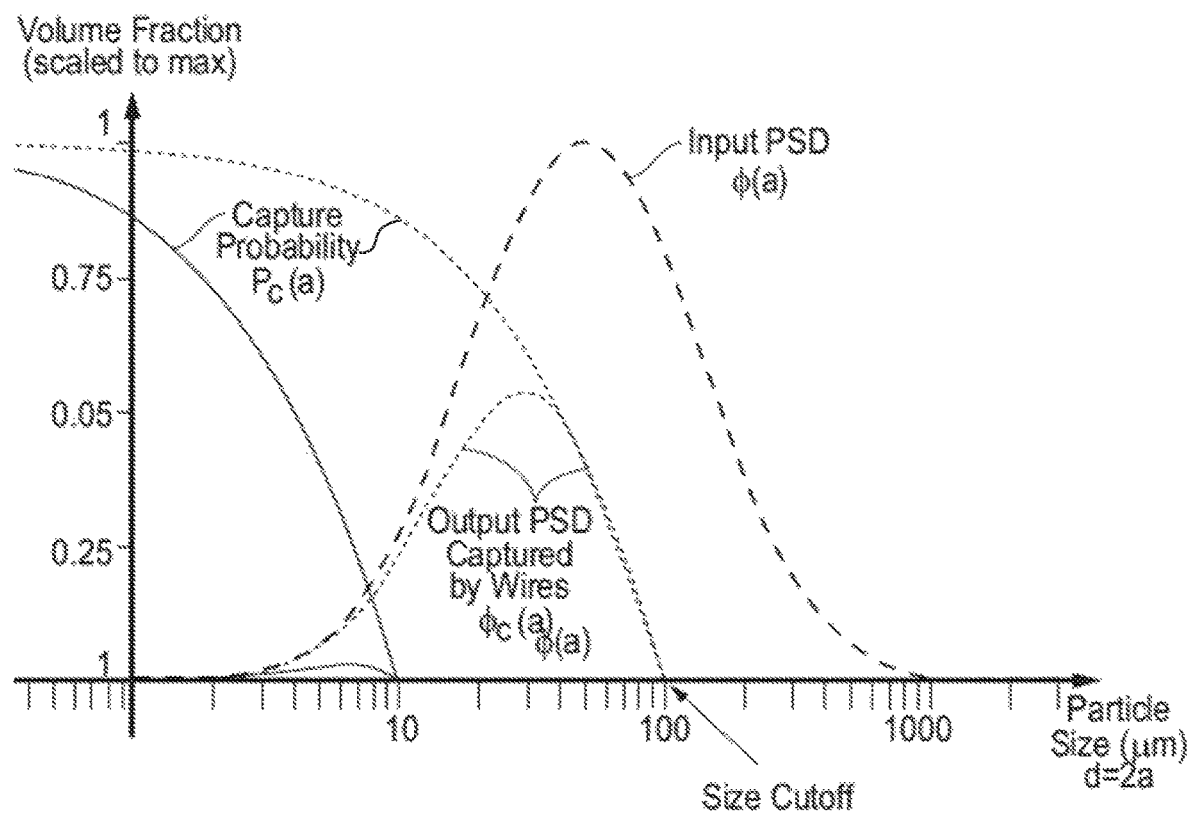
FIG. 20: includes a graph illustrating PSD before and after particle separation according to one embodiment.

FIG. 20 illustrates embodiments, wherein the filtering process can be designed that particles with a cutoff size of 10 μm or particles with a cutoff size of 100 μm can be separated by varying the conditions of the process.

The filtering method of the present disclosure can be conducted with a high efficiency and high selectivity with regard to a desired separated particle size range. In comparison to other existing filtering methods, for example, sedimentation or passing the dispersion through a filter, the method of the present disclosure can be conducted faster and more exact concerning a desired particle separation.

Many different aspects and embodiments are possible. Some of those aspects and embodiments are described herein. After reading this specification, skilled artisans will appreciate that those aspects and embodiments are only illustrative and do not limit the scope of the present invention. Embodiments may be in accordance with any one or more of the embodiments as listed below.

EMBODIMENTS

Embodiment 1

A filtering process comprising:
providing a dispersion comprising a liquid and a plurality of particles contained in the liquid;
moving an object relative to the dispersion; selectively removing at least a portion of the plurality of particles from the dispersion to obtain a plurality of separated particles attached to the object; and removing the separated particles from the object.

Embodiment 2

A filtering process comprising: providing a dispersion comprising a liquid and a plurality of particles contained in the liquid; moving an object relative to the dispersion; and controlling at least one parameter selected from the group consisting of a viscosity of the dispersion; a surface tension of the dispersion; a moving speed of the object; a shape of the object; and and a dimension of the object, wherein controlling is conducted to selectively remove at least a portion of the plurality of particles from the dispersion to obtain a plurality of separated particles attached to a surface of the object.

Embodiment 3

A filtering process comprising: providing a dispersion comprising a liquid, a first plurality of particles contained in the liquid, and a second plurality of particles contained in the liquid, the second plurality of particles being distinct from the first plurality of particles based upon at least one characteristic selected from the group consisting of average particle size (D50), D90 particle size, D90–D10 value, particle shape, and chemical composition of the particles; moving an object through the dispersion; and controlling at least one parameter selected from the group consisting of viscosity of the dispersion, surface tension of the dispersion, moving speed of the object, shape of the object, and dimension of the object, wherein controlling is conducted to selectively remove from the dispersion at least a portion of the first plurality of particles or at least a portion of the second plurality of particles to obtain a plurality of separated particles attached to a surface of the object.

Embodiment 4

The filtering process of Embodiments 1, 2, or 3 wherein the process is a continuous process.

Embodiment 5

The filtering process of Embodiments 2 or 3, wherein the process further includes removing the plurality of separated particles from the surface of the object.

Embodiment 6

The filtering process of Embodiments 1 or 5, wherein removing the plurality of separated particles from the surface of the object includes drying the surface of the object.

Embodiment 7

The filtering process of Embodiment 6, wherein removing the plurality of separated particles from the surface of the object includes washing the surface of the object with a collecting fluid, wherein the collecting fluid contains the separated particles after washing.

Embodiment 8

The filtering process of any of the preceding Embodiments, wherein moving includes pulling or pushing the at least one object out of the dispersion and forming a liquid film on the surface of the object including separated particles, the liquid film comprising a dynamic meniscus when leaving the dispersion.

Embodiment 9

The filtering process of any of the preceding Embodiments, wherein controlling includes adjusting at least one parameter selected from the group consisting of the viscosity of the dispersion, the surface tension of the dispersion, the moving speed of the object, the shape of the object, the dimension of the object, or any combination thereof.

Embodiment 10

The filtering process of Embodiment 9, wherein adjusting includes:
measuring at least one parameter during moving of the object through the dispersion and generating a measurement value; and changing at least one parameter during moving of the object through the dispersion based on the measurement value.

Embodiment 11

The filtering process of Embodiment 10, wherein the measurement value is at least one of a viscosity value, a surface tension value, a moving speed value, a shape value, a dimension value, or any combination thereof.

Embodiment 12 the filtering process of embodiment 10, wherein the measurement value includes a cutoff size of the plurality of separated particles.

Embodiment 13

The filtering process of Embodiment 10, further comprising calculating a capillary number based on a measurement value, and changing at least one parameter based on the capillary number.

Embodiment 14

The filtering process of Embodiment 10, wherein the measurement value is associated with a thickness of a film formed on the object and at least one parameter is changed based on the measurement value associated with the thickness of the film.

Embodiment 15

The filtering process of any of the preceding Embodiments, wherein a cutoff size of the plurality of separated particles during filtering is at least 1 µm, such as at least 3 µm, at least 5 µm, at least 10 µm, or at least 15 µm, and not greater than 1000 µm, such as not greater than 800 µm, not greater than 500 µm, not greater than 300 µm, not greater than 100 µm, not greater than 50 µm, not greater than 30 µm, or not greater than 20 µm.

Embodiment 16

The filtering process of any of the preceding Embodiments, wherein the moving speed of the object is at least 0.0005 m/s, such as at least 0.001 or at least 0.002 m/s, and not greater than 3 m/s, such as not greater than 2.2 m/s, or not greater than 1.0 m/s.

Embodiment 17

The filtering process of any of the preceding Embodiments, wherein the viscosity of the dispersion is at least 0.2 cP, such as at least 0.3 cP, or at least 0.4 cP, and not greater than 6 cP, such as not greater than 5 cP, not greater than 4 cP, not greater than 3 cP, or not greater than 2 cP.

Embodiment 18

The filtering process of any of the preceding Embodiments, wherein the surface tension of the dispersion is not greater than 100 mN/m, such as not greater than 80 mN/m, or not greater than 50 mN/m, and at least 10 mN/m, such as at least 15 mN/m or at least 20 mN/m.

Embodiment 19

The filtering process of any of the preceding Embodiments, wherein a capillary number Ca during moving is at least 0.0001, such as at least 0.0002, or at least 0.001, and not greater than 0.04, such as not greater than 0.03, not greater than 0.02, or not greater than 0.015.

Embodiment 20

The filtering process of any of the preceding Embodiments, wherein the at least one object includes a wire, a belt, a sheet, a woven mat, a non-woven mat, or a fiber.

Embodiment 21

The filtering process of Embodiment 20, wherein the at least one object includes a plurality of wires.

Embodiment 22

The filtering process of Embodiment 21, wherein an average radius of the plurality of wires is at least 20 µm, such as at least 30 µm, or at least 50 µm, and not greater than 1500 µm, such as not greater than 1200 µm, not greater than 1000 µm, or not greater than 800 µm.

Embodiment 23

The filtering process of any of Embodiments 1, 2, or 4-22, wherein an amount of the plurality of solid particles in the dispersion is at least 0.1 vol %, such as at least 0.2 vol %, at least 0.4 vol %, at least 0.8 vol %, at least 1 vol %, at least 5 vol %, or at least 10 vol %, and not greater than 50 vol %, such as not greater than 45 vol %, not greater than 30 vol %, not greater than 25 vol %, not greater than 20 vol % or not greater than 15 vol %.

Embodiment 24

The filtering process of Embodiment 22 or 23, wherein the wires have an average radius SRW and the plurality of filtered particles have a cutoff size Pc, and a ratio of SRW to PC is not greater than 1:0.8, such as not greater than 1:0.7, such as not greater than 1:0.6, or not greater than 1:0.5, and at least 1:0.2, such as at least 1:0.1 or at least 1:0.05.

Embodiment 25

The filtering process of any of Embodiments 1, 2, or 4-24, wherein the plurality of particles has an average particles size (D50) of at least 1 μm, such as at least 3 μm, at least 5 μm, or at least 10 μm, and not greater than 1000 μm, such as not greater than 500 μm, not greater than 200 μm, not greater than 100 μm, not greater than 50 μm, not greater than 30 μm, or not greater than 20 μm.

Embodiment 26

The filtering process of any of Embodiments 1, 2, or 4-25, wherein the plurality of particles have a D90 particles size of at least 2 μm, such as at least 5 μm, or at least 10 μm, and not greater than 2000 μm, such as not greater than not greater than 1500 μm, not greater than 1000 μm, not greater than 800 μm, not greater than 500 μm, not greater than 300 μm, or not greater than 200 μm.

Embodiment 27

The filtering process of any of Embodiments 1, 2, or 4-26, wherein a particle size range of D90–D10 of the plurality of particles is at least 5 μm, such as at least 8 μm, a least 10 μm, at least 15 μm, at least 20 μm, at least 30 μm, at least 50 μm, or at least 100 μm, and not greater than 2000 μm, such as not greater than 1500 μm, not greater than 1000 μm, not greater than 800 μm, not greater than 500 μm, not greater than 300 μm, or not greater than 200 μm.

Embodiment 28

The filtering process of any of Embodiments 1, 2, or 4-27, wherein the plurality of particles includes abrasive particles or a biological material.

Embodiment 29

The filtering process of Embodiment 28, wherein the abrasive particles include a material selected from diamond, cubic boron nitride, silicon carbide, boron carbide, alumina, silicon nitride, tungsten carbide, zirconia, silica, ceria, or any combination thereof.

Embodiment 30

The filtering process of Embodiment 28, wherein the biological material includes platelets, red blood cells, white blood cells, macrophages, dendritic cells, proteins, viruses, bacteria, spores, or any combination thereof.

Embodiment 31

The filtering process of any of Embodiments 3-22, wherein the plurality of separated particles contains at least 80% particles of the first plurality of particles, such as at least 95%, at least 98%, at least 99%, at least 99.5%, or at least 99.9% based on a total number of separated particles.

Embodiment 32

The filtering process of any of Embodiments 3-22, or 31, wherein the first plurality of particles has a D90–D10 value of at least 1 μm and not greater than 12 μm; the second plurality of particles has a D90–D10 value of at least 15 μm and not greater than 200 μm; and the plurality of separated particles includes at least 99% from the first plurality of particles based on a total number of the plurality of separated particles.

Embodiment 33

The filtering process of any of Embodiments 3, 31, or 32, wherein the first plurality of particles has an average particle size SP1 and the second plurality of particles has an average particle size SP2, and a ratio of SP1 to SP2 is not greater than 1:2, such as not greater than 1:3, or not greater than 1:5 and at least 1:1.3 or at least 1:1.5.

Embodiment 34

The filtering process of any of Embodiments 3 or 31-33, wherein the first plurality of particles and the second plurality of particles include abrasive particles.

Embodiment 35

The filtering process of Embodiment 34, wherein the abrasive particles comprise a material selected from the group consisting of diamond, cubic boron nitride, silicon carbide, boron carbide, alumina, silicon nitride, tungsten carbide, zirconia, silica, ceria, or any combination thereof.

Embodiment 36

The filtering process of any of Embodiments 3 or 31-33, wherein the first plurality of particles and the second plurality of particles include particles of a biological material.

Embodiment 37

The filtering process of Embodiment 36, wherein the biological material includes platelets, red blood cells, white blood cells, macrophages, dendritic cells, proteins, viruses, spores, or any combination thereof.

Embodiment 38

The filtering method of any of Embodiments 3 or 31-37, wherein the first plurality of particles has a primary aspect ratio of length to width of not greater than 2 such as not greater than 1.7, or not greater than 1.5, and the second plurality of particles has a primary aspect ratio of at least 5, such as at least 10, or at least 15, or at least 20.

Embodiment 39

The filtering process of any of the preceding Embodiments, wherein a material of the at least one object includes a metal, an alloy, a polymer, a ceramic, or a combination thereof.

Embodiment 40

The filtering process of any of the preceding Embodiments, wherein the liquid includes water, an alcohol, an ester, an ether, a hydrocarbon, or any combination thereof.

Embodiment 41

The filtering process of any of the preceding Embodiments, wherein the dispersion further includes a surfactant, a pH modifier, a defoaming agent, a viscosity modifying agent, an anti-fungal agent, or any combination thereof.

Embodiment 42

A filtering process comprising:
providing a dispersion comprising a liquid and a plurality of particles contained in the liquid; moving at least one object relative to the bulk dispersion; and controlling at least one parameter selected from the group consisting of a viscosity of the dispersion, a surface tension of the dispersion, a moving speed of the at least one object,
a shape of the at least one object; and and a dimension of the at least one object,
wherein controlling is conducted to selectively remove the liquid from the dispersion on a surface of the object to obtain a separated liquid, the separated liquid being essentially free of the plurality of particles contained in the dispersion.

Embodiment 43

An assembly for separating particles from a dispersion, comprising:
a chamber including a dispersion, the dispersion comprising a liquid and a plurality of particles;
a movable object, the object being adapted for moving through the chamber and adsorbing at least a portion of the plurality of particles during moving;
a first construction adapted for moving the object relative to the dispersion at a controlled moving speed, and a second construction adapted for removing and collecting from the object a plurality of separated particles from the dispersion.

Embodiment 44

The assembly of Embodiment 43, wherein the movable object includes a plurality of wires, a belt, or a sheet.

Embodiment 45

The assembly of Embodiments 43 or 44, wherein the second construction includes a heater adapted for evaporating liquid from the object and drying the plurality of separated particles.

Embodiment 46

The assembly of Embodiments 43 or 44, wherein the second construction includes a brush or a knife.

Embodiment 47

The assembly of any of Embodiments 43-46, further including a tank for collecting the plurality of separated particles.

Embodiment 48

The assembly of Embodiments 43 or 44, wherein the second construction includes a liquid sprayer adapted for washing the plurality of separated particles from the object with a collecting fluid.

Embodiment 49

The assembly of Embodiment 48, further including a tank for receiving after washing the collecting fluid comprising separated particles.

Embodiment 50

The assembly of any of Embodiments 43 to 49, wherein the assembly is adapted for continuously separating particles from the dispersion.

Embodiment 51

The assembly of Embodiment 50, wherein the assembly is adapted for continuously receiving the dispersion and continuously moving the object through the dispersion for particle separation.

Embodiment 52

An article comprising an object and a plurality of separated particles, wherein the plurality of separated particles have been attached to the object by conducting the process of Embodiments 1, 2, or 3.

Embodiment 53

The articles of Embodiment 52, wherein the object is a sheet.

Embodiment 54

The article of Embodiment 53, wherein the object is a plurality of wires.

Embodiment 55

The article of any of Embodiments 52, 53, or 54, wherein the plurality of separated particles include a medical material selected from platelets, red blood cells, cell fractures, viruses, or bacteria.

Embodiment 56

The article of Embodiment 55, wherein the article is part of a diagnostic kit.

Embodiment 57

The article of Embodiments 52, 53, or 54, wherein the separated particles are abrasive particles.

Embodiment 58

The filtering process of any of Embodiments 1-41, further including using a pre-determined algorithm to calculate the moving speed of the object for obtaining a desired cutoff size of the plurality of separated particles, the cutoff size corresponding to a thickness of a dynamic meniscus at a stagnation point h*, the dynamic meniscus being formed along a moving surface of the object when leaving the dispersion.

EXAMPLES

The following non-limiting examples illustrate the present invention.

Examples 1-5

Cylindrical Wire Filtering of dispersions containing abrasive particles in different liquids. A plurality of 1000 stainless steel wires having a radius of 60 μm is moved through an aqueous dispersion containing 0.4 vol % alumina particles. All examples are conducted at a temperature of 25° C., except in Example 2, wherein water is heated to a temperature of 90° C. The alumina particles contained in the dispersion have a D10 to D90 particles size from 1 μm to 1000 μm. The liquids next to water are acetone (Example 3), toluene (Example 4), and Hexane (Example 5). The wires are vertically pulled out of the dispersion at a pre-calculated wire speed for each type of dispersion, see Table 1. The wire speed was calculated based on a theoretical model involving equations (1) to (6), and designed to remove particles with the liquid film on the wires having a cutoff size of 12 μm. For the calculations, as input parameters were used known parameters of the dispersions and the objects, such as the viscosity of the liquids, surface tension of the liquids, the wire radius, the number of wires, and the solid particle volume fraction in the liquid dispersion prior to filtering.

After the wires are pulled out of the dispersion, the liquid films containing alumina particles with a maximum particle size of 12 μm (i.e., the cutoff size) are removed from the wires by infra-red drying and shaking the wires, such that the particles fall into a collection container.

Next to the moving speed of the wire (wire speed), the mathematical model could also calculate output parameters such as the total fluid recovery rate and the total solid recovery rate during conducting the filtering process. A summary of all input and output parameters can be seen in Table 1.

Figure 21:
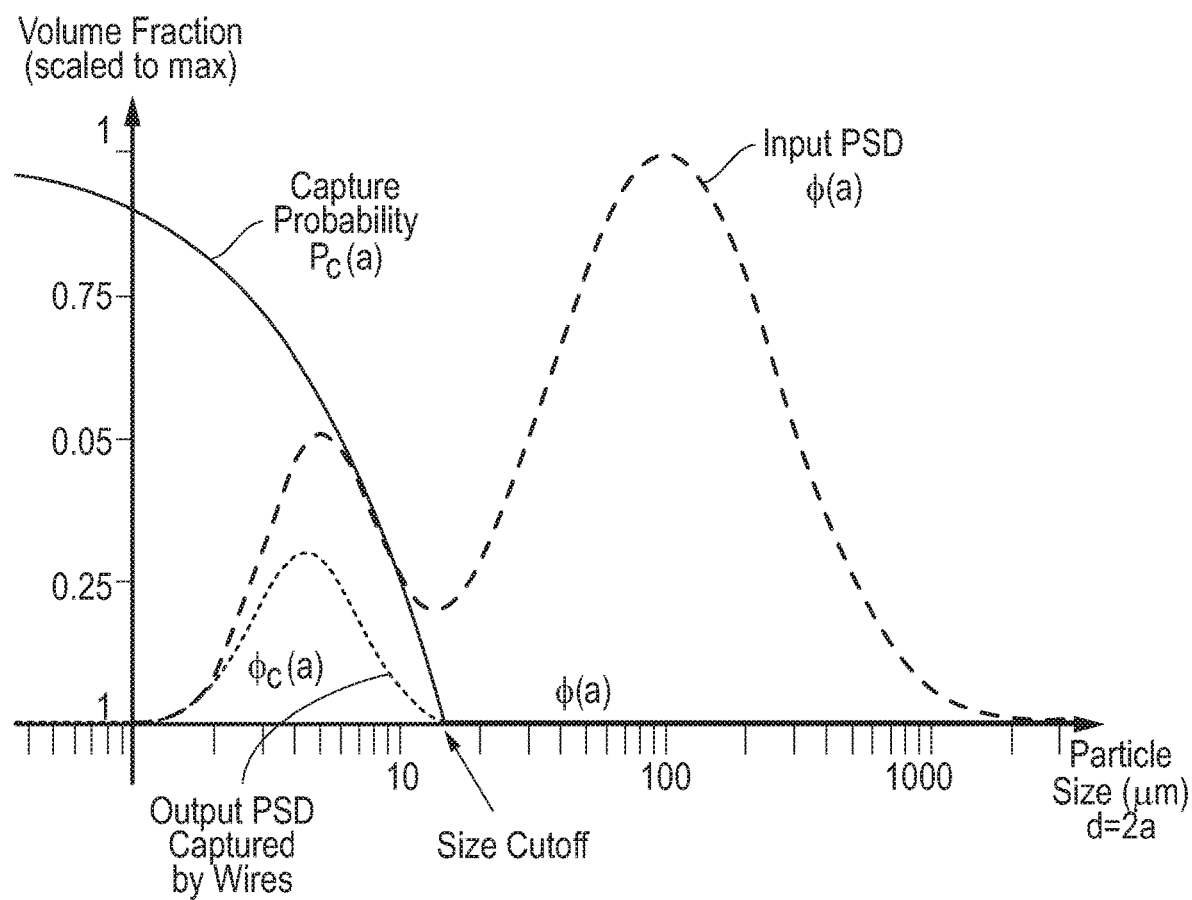
FIG. 21: includes a graph illustrating PSD before and after particle separation according to one embodiment.

FIG. 21 illustrates the particle size distribution (PSD) of the abrasive particles in the dispersion of Example 1 before filtering and after filtering. FIG. 21 further illustrates the particle distribution of the separated abrasive particles removed by the filtering process. The graph demonstrates that the separated particles do not contain particles having a larger particle size than 12 μm.

Example 6

Cylindrical Wire Filtering of Blood Sample.

A plurality of 10 stainless steel wires having a wire radius of 1000 μm is moved through a blood sample at a temperature of 25° C. Similar as in Examples 1-5, calculations were made to obtain the required wire speed for a cutoff size of separated particles at 10 μm, as well as the fluid recovery rate and the total solid recovery rate. Compared to the filtering of dispersions comprising abrasive particles in Examples 1-5, the filtering of the blood sample need to be conducted much slower, at a speed of 0.002 m/s. The blood particles in the thin blood film on the wires are removed by washing the wires with water under pressure and collecting the water and blood particles in a collection tank.

Figure 22:
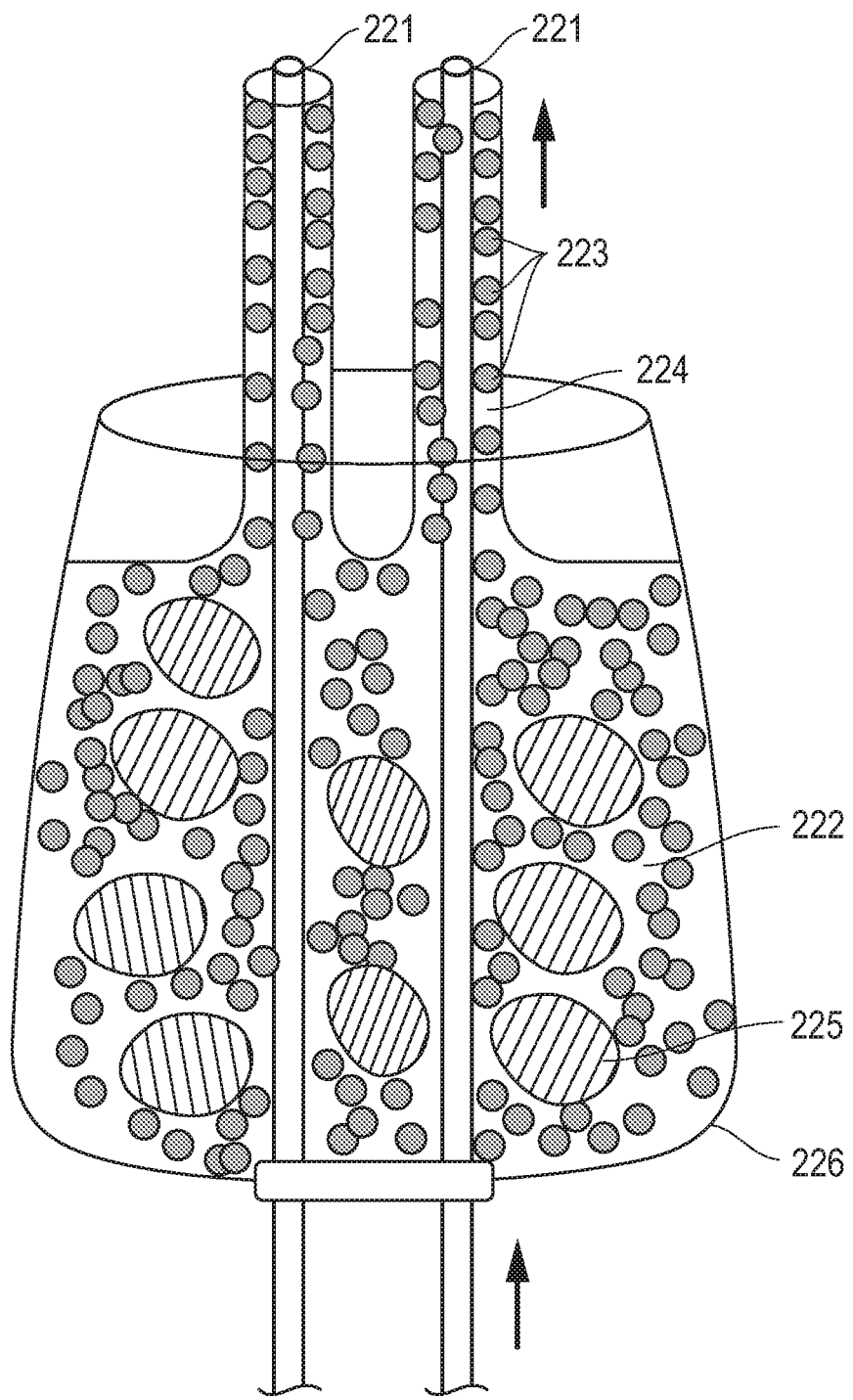
FIG. 22: includes an illustration of an assembly for cell sorting of a biomedical sample according to one embodiment.

An illustration of the filtering of a blood sample is shown in FIG. 22. The wires (221) are moved through a blood dispersion (222). The separated particles (223) contained in the film (224) on the wires removed from the blood sample are the small particles (with a size<h*), e.g., red blood cells, while larger particles (225), e.g., white blood cells, remain in the tank (226).

Figure 23:
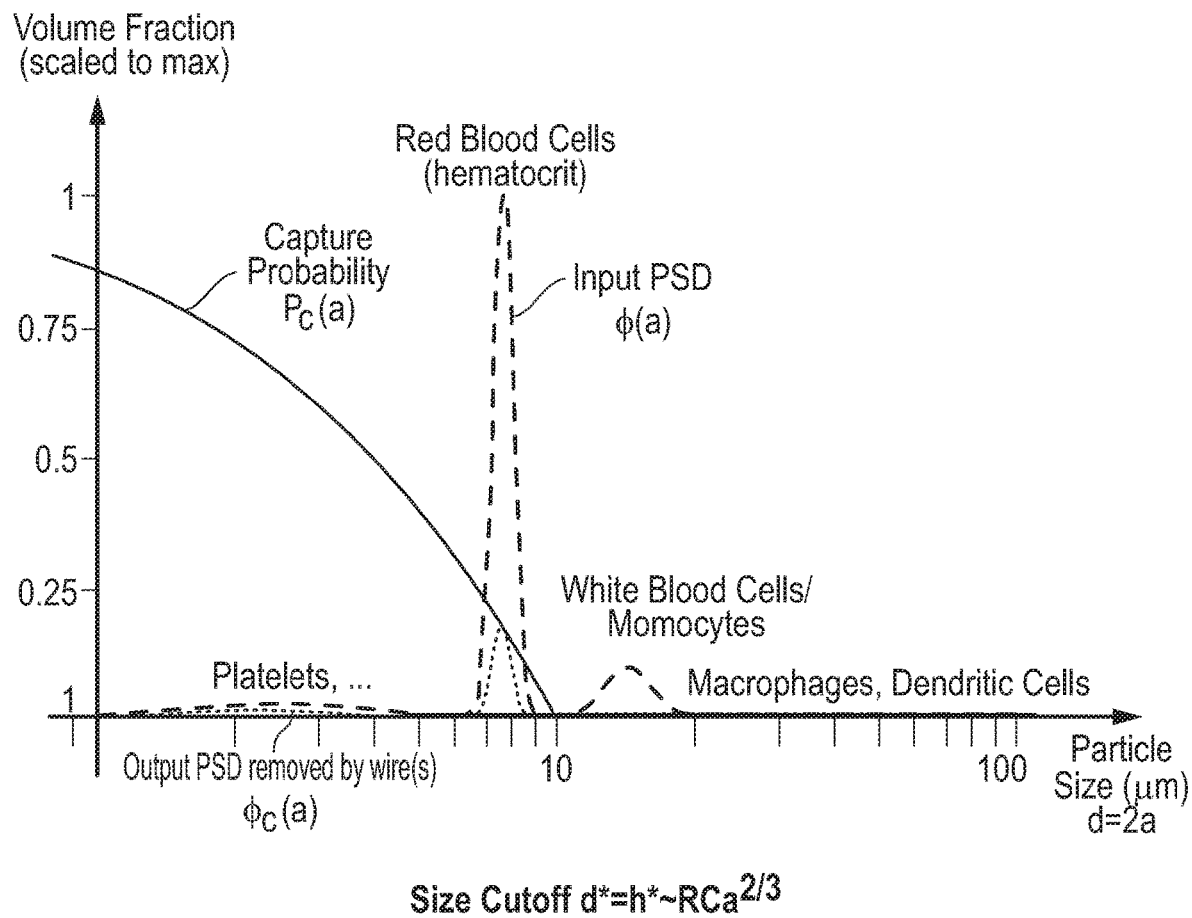
FIG. 23: includes a graph illustrating PSD before and after particle separation according to one embodiment.

FIG. 23 illustrates that by selecting process conditions which lead to a particle cutoff size of 10 μm, red blood cells (hematocrits) and platelets, which have a particle size smaller than 10 μm, can be separated by the filtering process from larger white blood cells, macrophages and dendritic cells. A summary of the calculated data is shown in Table 1.

Example 7

Cylindrical Wire Filtering of Whole Milk Sample

The wire filtering of a whole milk sample is conducted the same way as the experiments described for Examples 1-5. The calculations assumed that whole milk has a solid content of about 15% and filtering paramters were calculated for a cutoff particle size of 10 microns, which may exclude all oil globules and clusters of oil globules, and a fat-free milk can be obtained. A summary of the experimental conditions and calculated results for whole milk are shown in Table 1.

TABLE 1

| | Filtering Examples using wires as objects (Examples 1-7) | | | | | | |
|---|---|---|---|---|---|---|---|
| Example | Water [25° C.] 1 | Water [90° C.] 2 | Acetone [25° C.] 3 | Hexane [25° C.] 4 | Toluene [25° C.] 5 | Blood [25° C.] 6 | Whole Milk [20° C.] 7 |
| Viscosity of Dispersion [cP] | 1.79 | 0.62 | 0.62 | 0.60 | 1.13 | 4 | 3 |
| Pure liquid viscosity [cP] | 0.89 | 0.31 | 0.31 | 0.297 | 0.56 | 4 | 3 |
| Initial solid volume fraction | 0.2 | 0.2 | 0.2 | 0.2 | 0.2 | 0.45 | 0.15 |
| Surface tension [mN/m] | 72 | 60 | 23 | 18 | 28 | 56 | 43 |
| Capillary Speed [m/s] | 40.16 | 96.07 | 36.83 | 30.10 | 24.82 | 14 | 14.33 |
| Particle Size cutoff d* [μm] | 12 | 12 | 12 | 12 | 12 | 10 | 10 |

TABLE 1-continued

Filtering Examples using wires as objects (Examples 1-7)

| Example | Water [25° C.] 1 | Water [90° C.] 2 | Acetone [25° C.] 3 | Hexane [25° C.] 4 | Toluene [25° C.] 5 | Blood [25° C.] 6 | Whole Milk [20° C.] 7 |
|---|---|---|---|---|---|---|---|
| Wire radius [μm] | 60 | 60 | 60 | 60 | 60 | 1000 | 60 |
| Number of wires | 1000 | 1000 | 1000 | 1000 | 1000 | 10 | 1000 |
| Max. strain rate [1/s]] | 105035 | 251293 | 96329 | 78688 | 64917 | 538 | 34223 |
| Critical capillary number | 0.0314 | 0.0314 | 0.0314 | 0.0314 | 0.0314 | 0.00013 | 0.0314 |
| Flow rate per wire [mL/hr] | 13.68 | 32.73 | 12.55 | 10.25 | 8.45 | 1.17 | 3.09 |
| Solid filtration ratio | 0.3 | 0.3 | 0.3 | 0.3 | 0.3 | 0.5 | 0.3 |
| Wire speed [m/s] | 1.26 | 3.01 | 1.15 | 0.94 | 0.78 | 0.0065 | 0.342 |
| Total fluid recovery rate [L/hr] | 13.68 | 32.73 | 12.55 | 10.25 | 8.45 | 0.01168 | 3.09 |
| Total solid recovery rate [L/hr] | 0.821 | 1.964 | 0.753 | 0.615 | 0.507 | 0.0026 | 0.139 |

Examples 8-12

Flat Sheet Capillary Filtering of Dispersions Containing Abrasive Particles in Different Liquids.

Example 8-12 are conducted under the same conditions as Examples 1-5, except that the object is a flat sheet having a density of 1 g/cm3 and a width of 1 meter, and a cutoff value of 20 μm was selected. Theoretical calculations were made to obtain the needed sheet speed for pulling the sheet out of the dispersion for separating abrasive particles with a cutoff size of 20 μm. After the sheet is pulled out of the dispersion, the liquid film containing alumina particles with a maximum particle size of 20 μm (i.e., the cutoff size) are removed from the sheet by infra-red drying and blowing hot air on the sheet, such that the alumina particles fall into a collection container. A summary of the applied sheet speed for filtering dispersions with different types of liquid can be seen in Table 2

Example 13

Example 13 is conducted under the same conditions as Example 6, except that the object is a flat sheet having a density of 1.06 g/cm$^3$ and a width of 0.03 meters. Theoretical calculations were made to obtain the needed sheet speed for pulling the sheet out of the dispersion for separating particles contained in the blood with a cutoff size of 20 μm. A summary of all input and output parameters of the calculations can be seen in Table 2.

Example 14

Example 14, using whole milk as a dispersion, is conducted under the same conditions as Example 7, except that the object is a flat sheet having a density of 1.06 g/cm$^3$ and a width of 0.03 meters. A summary of the input and output data is shown in Table 2.

TABLE 2

Filtering Examples using a sheet as object (Examples 8-14)

| Example | Water [25° C.] 8 | Water [90° C.] 9 | Acetone [25° C.] 10 | Toluene [25° C.] 11 | Hexane [25° C.] 12 | Blood [25° C.] 13 | Whole Milk [20° C.] 14 |
|---|---|---|---|---|---|---|---|
| Viscosity of Dispersion [cP] | 1.79 | 0.62 | 0.62 | 1.13 | 0.59 | 4 | 3 |
| Pure liquid Viscosity [cP] | 0.89 | 0.31 | 0.31 | 0.56 | 0.297 | 4 | 3 |
| Initial solid volume fraction | 0.2 | 0.2 | 0.2 | 0.2 | 0.2 | 0.45 | 0.15 |
| Surface tension [mN/m] | 72 | 60 | 23 | 18 | 28 | 56 | 43 |
| Capillary speed [m/s] | 40.16 | 96.07 | 36.82 | 24.82 | 30.08 | 14.00 | 7.11 |
| Particle Size cutoff d* [μm] | 20 | 20 | 20 | 20 | 20 | 10 | 10 |
| Particle density Alumina [g/cm3] | 3.95 | 3.95 | 3.95 | 3.95 | 3.95 | | |
| Density of Dispersion [g/cm3] | 1.587 | 1.574 | 1.417 | 1.484 | 1.314 | 1.06 | 1.026 |

TABLE 2-continued

Filtering Examples using a sheet as object (Examples 8-14)

| Example | Water [25° C.] 8 | Water [90° C.] 9 | Acetone [25° C.] 10 | Toluene [25° C.] 11 | Hexane [25° C.] 12 | Blood [25° C.] 13 | Whole Milk [20° C.] 14 |
|---|---|---|---|---|---|---|---|
| Density of pure liquid [g/cm3] | 0.997 | 0.98 | 0.784 | 0.867 | 0.655 | | |
| Sheet density [g/cm3] | 1 | 1 | 1 | 1 | 1 | 1.06 | 1 |
| Sheet width [m] | 1 | 1 | 1 | 1 | 1 | 0.03 | 1 |
| Capillary length [mm] | 2.15 | 1.97 | 1.28 | 1.38 | 1.18 | 2.32 | 2.07 |
| Max. strain rate [1/s]] | 374.10 | 1019.6 | 741.54 | 446.25 | 687.86 | 90.09 | 100.17 |
| Critical capillary number | 0.04 | 0.04 | 0.04 | 0.04 | 0.004 | 0.0003 | 0.014 |
| Solid filtration ratio | 0.3 | 0.3 | 0.3 | 0.3 | 0.3 | 0.5 | 0.3 |
| Sheet speed [mm/s] | 7.48 | 20.39 | 14.83 | 8.93 | 13.76 | 1.08 | 1.40 |
| Total fluid recovery rate [mL/hr] | 179 712 | 489 92 | 355 | 214 4 | 330 | 0.47 | 12.0 |
| Total solid recovery rate [mL/hr] | 10.77 | 29.36 | 21.36 | 17.14 | 19.81 | 0.11 | 0.5 |

Mathematical Model for Calculating Particle Size Disctribution (PSD) of Separated Particles During Filtering A mathematical model has been developed which can predict the particle size distribution (PSD) of the particles maintained on the object with the removed liquid film. These predictions can be used for selecting appropriate process conditions in order to obtain a desired particle separation.

The mathematical model is centered on the parameters of the particle flow rate $\phi_c(a)$ (volume fraction of particles with radius a) and a given PSD of particles contained in an input dispersion $\phi(a)$. For non-spherical particles, a "radius a" was defined being half of the "film thickness diameter d" (d=2a) and as the shortest cross sectional distance, which must "fit" within the meniscus for an elongated particle to be captured in the liquid film on the object.

Figure 19A:
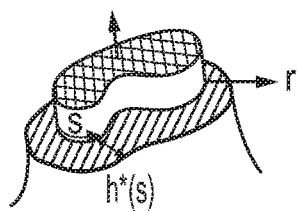
FIG. 19A, B, C, D, E includes graphs related to a probabilistic model with regard to the capture probability.
Figure 19B:
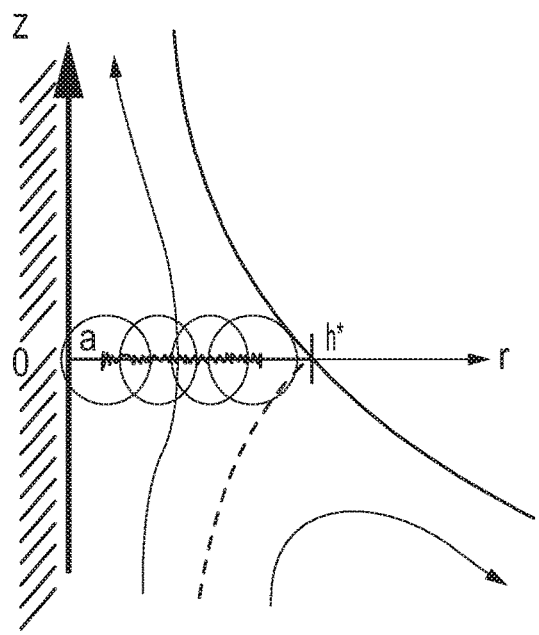
Figure 19C:
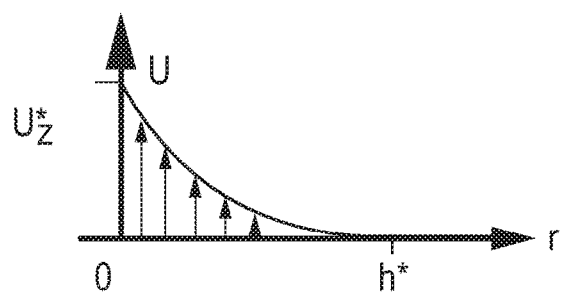

The theory relies on the probabilistic model illustrated in FIGS. 19A, 19B, 19C, 19D, and 19E. The mean total particle flow rate $Q_c(a)$ (particle volume/time) was calculated of particles of radius a entering the liquid film by integrating the mean axial flux density (in the z direction parallel to the solid surface) over a cross section of the fluid region in the plane perpendicular to the surface and passing through the stagnation curve r=h* (s) on the meniscus, $$Q_c(a)=\phi(a) \oint \int_0^{h^*(s)} u^*_z(r,s) p^*_c(r,s,a) g^*_s(r,s,a) dr\, ds \quad (7)$$

wherein r is the normal radial coordinate and s is a tangential arc length coordinate in a curvilinear coordinate system for the meniscus cross section as illustrated in FIGS. 19A and 19B; $u^*_z(r,s)$ is the axial velocity profile (FIG. 19C); $p^*_c(r,s,a)$ is the capture probability (FIG. 19D) and $g^*_s(r,s)$ the particle-surface pair correlation function (FIG. 19E) for a particle following a streamline passing through the point (r,s) in the liquid film, where r is the normal or radial distance from the solid surface and s is a coordinate measuring distance around the cross section perimeter of the liquid surface. For a given excess chemical potential energy $\mu(r,a)$, e.g., due to electrostatic forces or packing entropy, which depends on the distance from the solid surface, the equilibrium pair correlation can take the form $g^*_s(r,a)=e^{-\mu(r,a)/k_BT}$. Non-equilibrium effects for particles passing through the meniscus may need to be considered and incorporate in models of the excess chemical potential or particle-surface correlation function. The general expression for the particle flow rate, Eq. (7), can allow calculations for complex solid surface geometries, such as grooved plates (FIG. 7), having non-uniform meniscus thickness, and general particle-surface correlations.

For calculations of the PSD of the particles removed with the liquid film on the object according to the process of the present disclosure, equation (8) can be used. Equation (8) is a simplified version of equation (7) using a Cartesian radial coordinate, and assumes a symmetric cross section of either a flat sheet or a circular wire and a that a thin film is contained on the surface of the object. These assumptions may allow to neglect any surface curvature of the object:

$$Q_c(a) \approx \phi(a) P \int_0^{h^*} u^*_z(x) p^*_c(x,a) g^*_s(x,a) dx \quad (8)$$

Figure 19D:
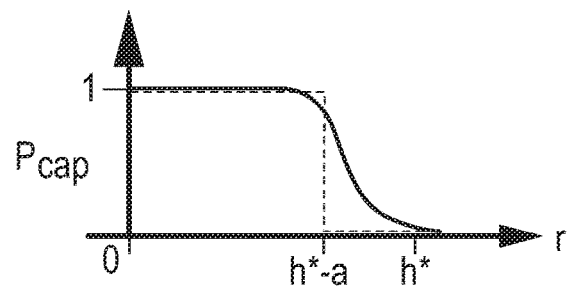
Figure 19E:
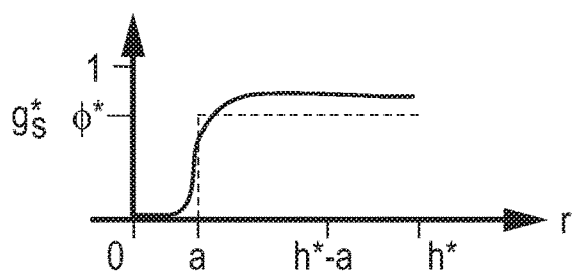

As indicated by the dashed curves in FIGS. 19D and 19E, it can be further assumed that $$p^*_c(r,a)=H(h^*-a-r) \quad (9)$$

and $$g^*_s(x,a) \approx \phi^*(a) H(x-a) \quad (10),$$

wherein H(x) is the Heaviside step function. Equation (9) generalizes the Collosqui-Morris-Stone criterion of Equation (1), by asserting that a particle entering the meniscus can be captured only if it "fits" inside the meniscus at the stagnation point h*. The Heaviside function in Equation (10) takes into account excluded volume near the surface (r<a), and the constant meniscus volume fraction $\phi^*(a)$ reflects long-range particle-surface forces.

With these assumptions, Equation (8) can be reduced to a radial integral over part of the velocity profile in the meniscus, see equation (11):

$$Q_c(a) \approx \phi(a) \phi^*(a) P \int_a^{h^*-a} u^*_z(r) dr \quad (11)$$

The flow profile at the stagnation point can be approximated as nearly parabolic and vanishing at the liquid surface $$u^*_z(x) \approx U\left(1-\frac{x}{h^*}\right)\left(1-\frac{x}{h_0}\right) \quad (12)$$

where the constant $h_0$ may be chosen as $$\frac{h^*}{h_0} = 3 - \frac{6h_f}{h^*} = 3(1 - 2\beta^{-1}) \quad (13)$$

in order to enforce mass conservation for the pure fluid going into the film.

$$\int_0^{h^*} u^*_z(x) dx = U h_f \quad (14)$$

Finally, Equation (12) can be substituted into Equation (11) and the integral performed to obtain the PSD in the coating as the desired result (volume fraction of particles of size a), $$\phi_c(a) = \frac{Q_c(a)}{Q_f} = \phi(a) f(\tilde{a}, \beta) H(1 - 2\tilde{a}) \quad (15)$$

The Heaviside function indicates a sharp size cutoff from Equation (1) applied independently to each particle arriving in the stagnation point region for filtering:

$$2\tilde{a} = \frac{2a}{h^*} = \frac{d}{h^*} < 1 \quad (16)$$

The function defining the ratio of final to initial PSD is $$f(\tilde{a},\beta) = \beta[1 - 2\tilde{a} - (2 - 3\beta^{-1})((1-\tilde{a})^2 - \tilde{a}^2) + (1 - 2\beta^{-1})((1-\tilde{a})^3 - \tilde{a}^3)] \quad (17)$$

For a flat plate, $\beta=3$, we can further simplify, $f(\tilde{a}, 3)=(1-\tilde{a})^3 - \tilde{a}^3$. The general formula in Equation (17) can be used for a cylinder much thinner than the capillary length with $\beta=3/2$. As expected, for any type of liquid film, all particles entering the meniscus can be entrained with 100% probability if the particle size is much smaller than the film thickness, $f(\tilde{a} \to 0, \beta) \to 1$. The filtration formula, Eq (15), is illustrated for different input PSDs in FIGS. 22 and 24.

The total solid volume fraction of particles in the coating is $$\phi_p = \int_0^\infty \phi_c(a) da \quad (18)$$

and the total solid flow rate (volume collected/time) is $$Q_s = \phi_p Q_f \quad (19)$$

The number of particles of size a entrained per area of the liquid film is given by $$n_p(a) = \frac{h_p(a)}{V_p(a)} = \frac{\phi_c(a) h_f}{V_p(a)} \quad (20)$$

where $V_p(a) = 4/3 \pi a^3$ for spherical particles.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of the invention.

What is claimed is:

1. A filtering process comprising:
   providing a dispersion comprising a liquid and a plurality of particles contained in the liquid;
   moving an object relative to the dispersion;
   controlling at least one parameter selected from the group consisting of
   a viscosity of the dispersion;
   a surface tension;
   a moving speed of the object;
   a shape of the object; or
   a dimension of the object; and
   selectively removing from the dispersion a plurality of separated particles attached to a surface of the object, wherein an average particle size of the plurality of separated particles is smaller than an average particle size of the plurality of particles of the dispersion before conducting the filtering process.

2. The filtering process of claim 1, wherein the process further includes removing the plurality of separated particles from the surface of the object.

3. The filtering process of claim 1, wherein the process is a continuous process.

4. The filtering process of claim 1, wherein the moving includes pulling or pushing the object out of the dispersion and forming a liquid film on the surface of the object including the plurality of separated particles, the liquid film comprising a dynamic meniscus when leaving the dispersion.

5. The filtering process of claim 4, wherein a cutoff size of the plurality of separated particles corresponds to a thickness of the dynamic meniscus at a stagnation point h*.

6. The filtering process of claim 1, wherein a cutoff size of the plurality of separated particles during filtering is at least 5 μm and not greater than 1000 μm.

7. The filtering process of claim 1, wherein the object includes a wire, a belt, a sheet, a woven mat, a non-woven mat, or a fiber.

8. The filtering process of claim 7, wherein the object includes a plurality of isolated wires.

9. The filtering process of claim 1, wherein the plurality of particles includes abrasive particles or a biological material.

10. The filtering process of claim 1, wherein the plurality of particles includes a first plurality of particles and a second plurality of particles, a D90–D10 value of the first plurality of particles is smaller than a D90–D10 value of the second plurality of particles, and at least 95% of the plurality of separated particles are particles of the first plurality of particles.

11. The filtering process of claim 10, wherein
   the first plurality of particles has the $D_{90}$–$D_{10}$ value of at least 1 μm and not greater than 12 μm;
   the second plurality of particles has the $D_{90}$–$D_{10}$ value of at least 15 μm and not greater than 200 μm; and
   the plurality of separated particles includes at least 99% from the first plurality of particles based on a total number of the plurality of separated particles.

12. The filtering process of claim 1, wherein the removing of the separated particles is at least partially based on capillary force between the dispersion and the solid surface of the object.

13. The filtering process of claim 1, wherein a cutoff-size of the plurality of separated particles is at least 1 μm and not greater than 100 μm.

14. The filtering process of claim 1, wherein a capillary number Ca during moving is at least 0.0001 and not greater than 0.04.

15. The filtering process of claim 1, wherein the object comprises a plurality of isolated wires have an average radius SRW, and the plurality of separated particles have an average particle size PC, and a ratio of SRW to PC ranges from 1:0.8 to 1:0.05.

16. The filtering process of claim 4, wherein the controlling includes controlling a thickness of the liquid film on the surface of the object including the plurality of separated particles.

17. A filtering process comprising:
  providing a dispersion comprising a liquid and a plurality of particles contained in the liquid;
  moving at least one object relative to the dispersion;
  controlling at least one parameter selected from the group consisting of a viscosity of the dispersion, a surface tension of the dispersion, a moving speed of the at least one object, a shape of the at least one object; and a dimension of the at least one object; and
  removing from the dispersion at least a portion of the liquid by forming a liquid film on a surface of the at least one object, wherein the liquid film on the surface of the at least one object being essentially free of the plurality of particles contained in the dispersion.

* * * * *